(12) United States Patent
Veljkovic et al.

(10) Patent No.: US 11,839,650 B2
(45) Date of Patent: Dec. 12, 2023

(54) UNIVERSAL INFLUENZA VACCINE TARGETING VIRUS/HOST RECOGNITION

(71) Applicant: THE BOARD OF REGENTS OF THE UNIVERSITY OF TEXAS SYSTEM, Austin, TX (US)

(72) Inventors: Veljko Veljkovic, Belgrade (RS); Slobodan Paessler, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 131 days.

(21) Appl. No.: 16/483,103

(22) PCT Filed: Feb. 2, 2018

(86) PCT No.: PCT/US2018/016690
§ 371 (c)(1),
(2) Date: Aug. 2, 2019

(87) PCT Pub. No.: WO2018/144903
PCT Pub. Date: Aug. 9, 2018

(65) Prior Publication Data
US 2019/0351046 A1 Nov. 21, 2019

Related U.S. Application Data

(60) Provisional application No. 62/453,650, filed on Feb. 2, 2017.

(51) Int. Cl.
*A61K 39/145* (2006.01)
*C07K 14/005* (2006.01)

(52) U.S. Cl.
CPC .......... *A61K 39/145* (2013.01); *C07K 14/005* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

2010/0285982 A1* 11/2010 Golding ................. A61K 39/12
435/7.1

OTHER PUBLICATIONS

Vejkovic et al. (Journal of Peptide research 2003, p. 158-166).*
Veljkovic et al. BMC Structural Biology, 2009, p. 1-10).*
Veljkovic et al. (Vaccine, 2014, p. 6569-6575).*

* cited by examiner

*Primary Examiner* — Agnieszka Boesen

(57) ABSTRACT

The present application generally relates to the development of a universal influenza vaccine, or production of antibodies, capable of providing broad protection against various strains of the flu, using an informational spectrum method (ISM) to identify the common structural characteristics of influenza antigens.

8 Claims, 4 Drawing Sheets

Figure 1:
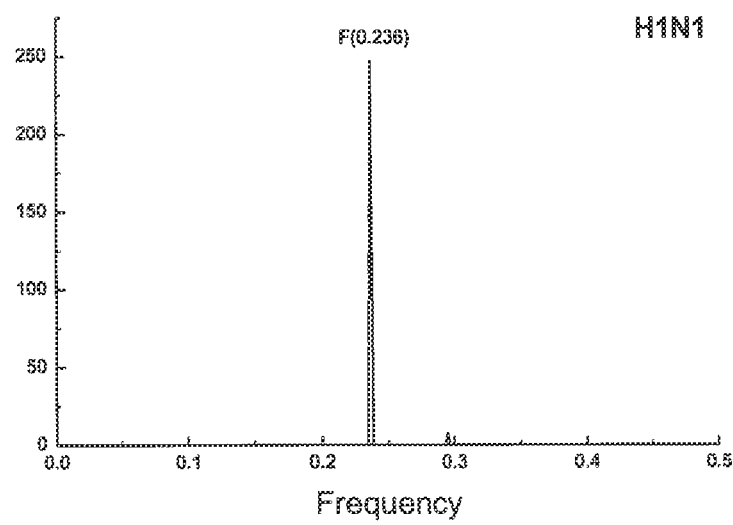
Figure 1:
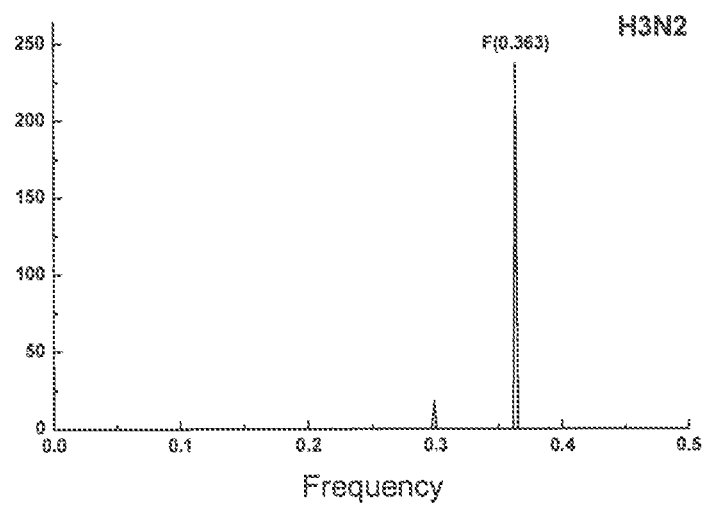
Figure 1:
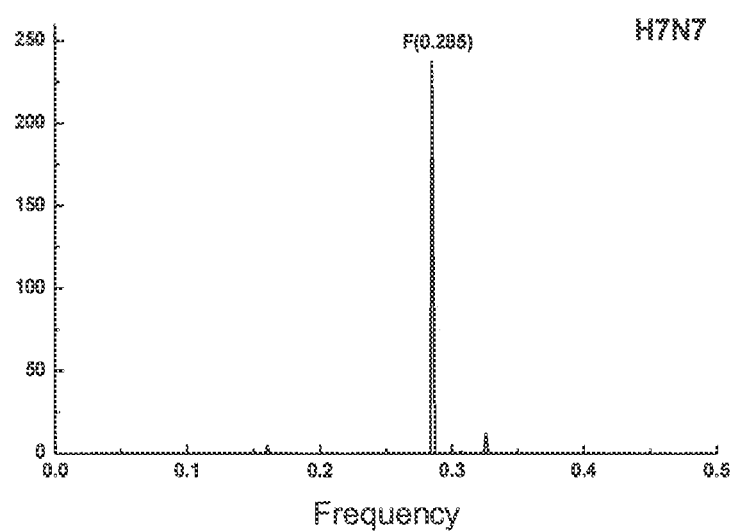
Figure 1:
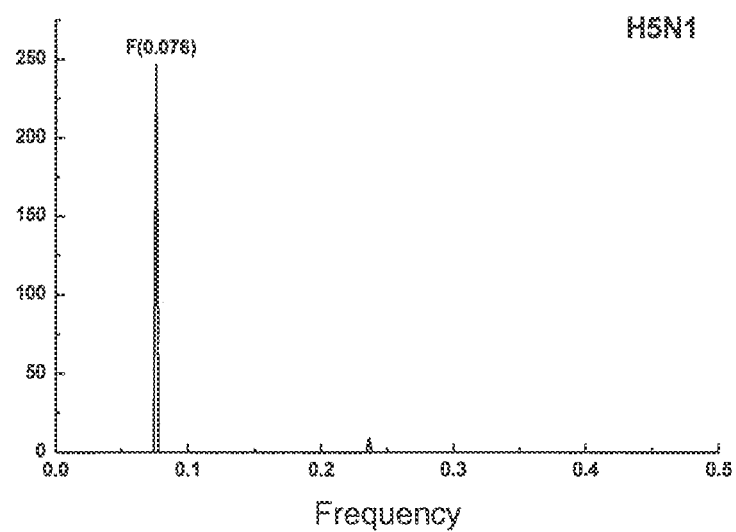

Specification includes a Sequence Listing.

A.

B.

C.

D.

FIGURE 3

A.

HA1 from A/Hong Kong/213/03 (H5N1)

DQICIGYHANNSTEQVDTIMEKNVTVTHAQDILEKTHNGKL**CDLDGVKPLILRDCSVAG
WLLGNPMCDEFINVPE**WSYIVEKANPANDLCYPGDFNDYEELKHLLSRINHFEKIQIIPK
NSWSSHEASLGVSSACPYQGKSSFFRNVVWLIKKNNAYPTIKRSYNNTNQEDLLVLWGIHHP
NDAAEQTRLYQNPTTYISVGTSTLNQRLVPKIATRSKVNGQNGRMEFFWTILKPNDAINFES
NGNFIAPEYAYKIVKKGDSAIMKSELEYGNCNTKCQTPMGAINSSMPFHNIHPLTIGECPKY
VKSNRLVLATGLRNSPQRERRRKKR

B.

UNIVERSAL INFLUENZA VACCINE TARGETING VIRUS/HOST RECOGNITION

RELATED APPLICATIONS

This application is a 371 National Stage filing of PCT/US2018/016690 filed Feb. 2, 2018 which claims priority to U.S. Provisional No. 62/453,650 filed on Feb. 2, 2017 the contents of each application is incorporated herein by reference in its entirety.

REFERENCE TO SEQUENCE LISTING

A sequence listing required by 37 CFR 1.821-1.825 is being submitted electronically with this application. The sequence listing is incorporated herein by reference. The sequence listing that is contained in the file named "UTMBP0398US_ST25" which is 61 KB (as measured in Microsoft Windows®) and was created on Apr. 19, 2022.

FIELD OF THE INVENTION

The invention generally relates to the development of a universal influenza vaccine capable of providing broad protection against different strains of the flu as well as the production of antibodies to treat the flu. More particularly, the invention related to the use of an information spectrum method (ISM) to identify novel peptides sharing structural homology with hemagglutinin (HA) from different influenza A and/or influenza B subtypes, and vaccines comprising the HA multi-epitope peptide antigen that is capable of eliciting cross-protective immunity against several different influenza A and/or influenza B subtypes. The universal flu vaccine can be used alone or in combination with strain-specific seasonal flu vaccines.

BACKGROUND OF THE INVENTION

Influenza, commonly called the flu, is a contagious respiratory illness caused by influenza viruses, which infect the respiratory tract. Fever, chills, fatigue, body aches, sore throat, and headache are common symptoms of flu. Unlike many other viral respiratory infections, such as the common cold, the flu can cause severe and life-threatening complications in some people, such as elderly, young children, pregnant women, and people with certain health conditions, e.g., congestive heart failure, asthma, or diabetes. An influenza season usually strikes both the northern and southern hemispheres each year, resulting in three to five million cases of severe illness and up to 500,000 deaths annually. It is estimated that in the United States, each year on average 5% to 20% of the population gets the flu and more than 200,000 people are hospitalized from seasonal flu-related complications. According to the Centers for Disease Control and Prevention, the best way to prevent the flu is by getting vaccinated each year.

Flu vaccines protect against the influenza viruses that research indicates will be most common during the upcoming season. Traditional flu vaccines, called trivalent vaccines, are made to protect against three flu viruses: an influenza A (H1N1) virus, an influenza A (H3N2) virus, and an influenza B virus. There are also flu vaccines made to protect against four flu viruses, called quadrivalent vaccines, which protect against the same viruses as the trivalent vaccine and an additional B virus. However, if the selected strain(s) do not match the strains spreading in the community and/or the strain(s) mutates prior to or during the flu season, that season's vaccine may not provide protection, the most recent example being the 2009 outbreak of H1N1 of swine origin. Thus, the protective capability of currently available influenza vaccines is substantially limited.

Three subtypes of influenza viruses, Type A, Type B, and Type C, affect humans, with influenza A and B viruses being the most common causes of influenza in humans. Influenza A, B and C are very similar in overall structure and composition: a viral envelope containing two main types of glycoproteins, hemagglutinin (HA) and neuraminidase (NA), wrapped around a central core that contains the viral RNA genome and other viral proteins that package and protect the RNA.

HA mediates binding of the virus to target cells and entry of the viral genome into the target cell, while NA is involved in the release of progeny virus from infected cells, by cleaving sugars that bind the mature viral particles. Thus, these proteins are used as targets for antiviral drugs and antigens to which antibodies can be raised. However, the two major surface glycoprotein antigens, HA and NA, are also most susceptible to change. For example, there are 16 immune classes of HA and 9 different NA classes that provide the basis for the different influenza virus subtypes like H1N1 or H3N2. H 1, 2 and 3, and N 1 and 2 are commonly found in humans.

Influenza viruses have two important immunological characteristics that present a challenge to vaccine preparation. The first concerns genetic changes that occur in the surface glycoproteins, e.g., HA and NA, every few years in a process known as "antigenic drift". A high number of mutations results from the error-prone RNA-dependent RNA polymerase during viral replication. The antigenic change produces viruses that elude resistance elicited by existing vaccines. The second characteristic of public health concern is that influenza viruses, in particular influenza A virus, can exchange genetic material and merge in a process known as "antigenic shift", which results in new strains that are different from both parent viruses. For example, influenza virus may emerge from avian or swine reservoirs and evolve into viruses that are efficiently transmitted among humans. These new, different strains can be lethal pandemic strains. Due to these changes, flu vaccines need to be modified at least every few years.

Influenza antigens and vaccines based thereon are known in the art. See, e.g., U.S. Pat. No. 9,051,369, U.S. 2012/0156242, Zhang et al. (2013) *Antiviral Res* 99(2):91-9, and Iba et al. (2014) *J Virol.* 88(13):7130-44, all of which relate to conserved neutralizing epitopes of HA1; U.S. Pat. Nos. 6,740,325 and 8,747,861 relating to multi-epitope peptide-based vaccines; and WO 1993/20846 and WO 2007/066334 relating to cross-strain influenza vaccines. However, challenges to a universal flu vaccine remain as a result of issues with high variability (such as the globular region of HA1), low immunogenicity, incomplete protective efficacy against hetero-typic strains, and adverse effects in human subjects, e.g., vaccine-induced enhancement of viral disease, high fever, and transient heart effects.

Accordingly, the identification of novel antigens that combine epitopes from several different influenza viruses and, thus, are capable of eliciting an immune response against various influenza viruses to provide cross-strain (or universal) protection against different flu strains is desirable.

SUMMARY OF THE INVENTION

The invention provides a method for identifying novel antigens possessing structural homology with HA from various influenza viruses and, thus, capable of eliciting an immune response against different strains of the flu. Such antigens can be used as the basis for a universal flu vaccine, suitable for use alone or in combination with traditional strain-specific, seasonal flu vaccines.

In one aspect, the invention provides a method of eliciting an immune response by administering an immunologic composition comprising a synthetic peptide having an informational spectrum (IS) that overlaps with the IS of at least one hemagglutinin (HA) protein or fragment thereof, wherein the synthetic peptide is capable of eliciting an immune response against the HA protein or fragment thereof. The at least one HA protein and the synthetic peptide may be homologous such that the synthetic peptide is suitable for use as an antigen to produce antibodies, preferably neutralizing antibodies, that bind to the at least one HA protein or fragment thereof.

The at least one HA protein or fragment thereof may be derived from one or more of influenza A virus subtype H1-H16. Alternatively, the at least one HA protein or fragment thereof may be derived from each of influenza A virus subtype H1-H16.

The HA protein or fragment thereof may be from a human influenza virus. In this instance, the HA protein or fragment thereof may be HAL HA2, and/or HA3. Alternatively, the at least one HA protein or fragment thereof may be from an avian influenza virus and/or a swine influenza virus. In this instance, the HA protein or fragment thereof is HAL HA2, HA3, HA4, HA5, and/or HA9.

A cross-spectrum (CS) based on the IS of the at least one HA protein or fragment thereof (determined using an ISM approach as described herein and generally understood in the art at the time of filing) and the IS of the synthetic peptide may contain a frequency component of F(0.148). The IS of the synthetic peptide may contain a frequency component of F(0.055), F(0.077), F(0.085), F(0.148), F(0.164), F(0.237), F(0.283), F(0.295), or F(0.364), where each frequency component may include a range of +/−0.001, 0.002, 0.003, 0.004, or 0.005. Additionally, the IS of the synthetic peptide may comprise F(0.145-0.149) and further contain at least 1, at least 2, at least 3, at least 4, at least 5, at least 6, at least 7, or all 8 of the frequency components selected from F(0.053-0.057), F(0.074-0.079), F(0.083-0.087), F(0.160-0.168), F(0.234-0.239), F(0.280-0.286), F(0.291-0.299), and F(0.362-0.366). The at least one HA protein or fragment thereof may be HA1 from influenza A virus subtype H1N1, H3N2, H7N7, and/or H5N1 and the IS of the particular HA1 may contain F(0.236), F(0.363), F(0.285), and/or F(0.076), respectively.

The synthetic peptide may comprise 15 to 350 amino acids. More particularly, the synthetic peptide may comprise 15 to 50 amino acids.

In one aspect, the synthetic peptide has a general formula of X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34 (SEQ ID NO:102), where X1 is Met, Ser, Gln or Cys; X2 is Asp; X3 is Val, Leu, Ile, Asn, Gly or Glu; X4 is Asp; X5 is Val, Leu, Ile, Asn or Gly; X6 is Val, Leu, Ile, Asn or Gly; X7 is Pro, His, Ala or Lys; X8 is Pro or His; X9 is Val, Leu, Ile, Asn or Gly; X10 is Val, Leu, Ile, Asn or Gly; X11 is Val, Leu, Ile, Asn or Gly; X12 is Thr, Phe or Arg; X13 is Asp; X14 is Met, Ser, Gln or Cys; X15 is Met, Ser, Gln or Cys; X16 is Val, Leu, Ile, Asn or Gly; X17 is Ala or Lys; X18 is Val, Leu, Ile, Asn, Gly or Glu; X19 is Trp or Tyr; X20 is Val, Leu, Ile, Asn or Gly; X21 is Val, Leu, Ile, Asn or Gly; X22 is Val, Leu, Ile, Asn, Gly or Glu; X23 is Val, Leu, Ile, Asn or Gly; X24 is Pro or His; X25 is Met, Ser, Gln or Cys; X26 is Met, Ser, Gln or Cys; X27 is Asp; X28 is Val, Leu, Ile, Asn, Gly or Glu; X29 is Thr, Phe or Arg; X30 is Val, Leu, Ile, Asn or Gly; X31 is Val, Leu, Ile, Asn or Gly; X32 is Val, Leu, Ile, Asn, Gly or Glu; X33 is Pro or His; and X34 is Val, Leu, Ile, Asn, Gly or Glu.

In another aspect, the synthetic peptide has a formula: Cys-Asp-X3-Asp-Gly-X6-X7-Pro-Leu-Ile-Leu-Arg-Asp-Cys-Cys-Val-Ala-X18-Tyr-Leu-Leu-X22-Asn-His-Ser-Cys-Asp-Val-Phe-Ile-X31-X32-Pro-X34 (SEQ ID NO:103), where X3, X6, X18, X22, X31, X32, and X34 are independently Val, Leu, Ile, Asn, Gly or Glu; and X7 is Pro, His, Ala or Lys.

In another aspect, the synthetic peptide has one of the following sequences:

```
CDEDGVKPLILRDCCVAGWLLGNHSCDVFINVPE

CDEDGVHPLILRDCCVAIYLLGNHSCDVFILVPE

CDEDGNHPLILRDCCVAIYLLNNHSCDVFILEPL

CDEDGIHPLILRDCCVAIYLLINHSCDVFILNPG

CDLDGLHPLILRDCSVANYLLINPMCDEFILEPL

SDGDINKPLLVTDSCNKNYLLNIHSCDVTNIIEN

QDLDINKPLLNTDQMLKNYLLNIPQQDLTNIIPN
```

In another aspect, the synthetic peptide has a general formula of X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34 (SEQ ID NO:104), where X1 is Gly or Glu; X2 is Val, Leu, Ile, Asn, Gly or Glu; X3 is Val, Leu, Ile, Asn or Gly; X4 is Ala or Lys; X5 is Pro, His, or Lys; X6 is Val, Leu, Ile, Asn or Gly; X7 is Val, Leu, Ile, Asn or Gly; X8 is Met, Ser, Gln or Cys; X9 is Thr, Phe or Arg; X10 is Val, Leu, Ile, Asn or Gly; X11 is Val, Leu, Ile, Asn or Gly; X12 is Pro, His, or Lys; X13 is Thr, Phe or Arg; X14 is Val, Leu, Ile, Asn, Gly or Glu; X15 is Pro, His, Ala or Lys; X16 is Val, Leu, Ile, Asn or Gly; X17 is Met, Ser, Gln or Cys; X18 is Val, Leu, Ile, Asn or Gly; X19 is Val, Leu, Ile, Asn or Gly; X20 is Pro or His; X21 is Ala or Lys; X22 is Val, Leu, Ile, Asn or Gly; X23 is Met, Ser, Gln or Cys; X24 is Trp or Tyr; X25 is Met, Ser, Gln or Cys; X26 is Asp; X27 is Pro or His; X28 is Val, Leu, Ile, Asn, Gly or Glu; X29 is Ala or Lys; X30 is Met, Ser, Gln or Cys; X31 is Val, Leu, Ile, Asn or Gly; X32 is Val, Leu, Ile, Asn, Gly or Glu; X33 is Met, Ser, Gln or Cys; and X34 is Met, Ser, Gln or Cys.

In another aspect, the synthetic peptide has one of the following sequences:

```
EELKKLLCRINKFEKISIIPKGSWSDHEACGVSC

EGLKHLLSRILHFIHIQIIPKNQYSDHIASGNSS

EGLKKLLCRIIKFGHISIIPKGMYSDHGACGESC

ENLKKLLCRLIKFNHISIIPKGQYSDHNACGGSC

EILKKLLCRLIKFIHISIIPKGQYSDHIACGNSC

GLVAPNVMTVLPTGKVMVLPAVQYMDPGAMVIMM

GGVAHVVCTVVHTGAVCVVPAVMWMDPGASVVMS
```

In yet another aspect, the synthetic peptide has a general formula of X1-X2-X3-X4-X5-X6-X7-X8-X9-X10-X11-X12-X13-X14-X15-X16-X17-X18-X19-X20-X21-X22-

X23-X24-X25-X26-X27-X28-X29-X30-X31-X32-X33-X34-X35-X36-X37-X38-X39-X40-X41-X42 (SEQ ID NO:105), where X1 is Val, Leu, Ile, Asn or Gly; X2 is Ala or Lys; X3 is Val, Leu, Ile, Asn, Gly or Glu; X4 is Val, Leu, Ile, Asn or Gly; X5 is Thr, Phe or Arg; X6 is Met, Ser, Gln or Cys; X7 is Val, Leu, Ile, Asn or Gly; X8 is Pro or His; X9 is Thr, Phe or Arg; X10 is Met, Ser, Gln or Cys; X11 is Val, Leu, Ile, Asn or Gly; X12 is Val, Leu, Ile, Asn, Gly or Glu; X13 is Pro or His; X14 is Pro or His; X15 is Val, Leu, Ile, Asn or Gly; X16 is Thr, Phe or Arg; X17 is Val, Leu, Ile, Asn or Gly; X18 is Val, Leu, Ile, Asn or Gly; X19 is Ala or Lys; X20 is Met, Ser, Gln or Cys; X21 is Pro or His; X22 is Ala or Lys; X23 is Trp or Tyr; X24 is Val, Leu, Ile, Asn or Gly; X25 is Ala or Lys; X26 is Met, Ser, Gln or Cys; X27 is Thr, Phe or Arg; X28 is Ala or Lys; X29 is Val, Leu, Ile, Asn, Gly, or Glu; X30 is Thr, Phe or Arg; X31 is Val, Leu, Ile, Asn or Gly; X32 Ala or Lys; X33 is Thr, Phe or Arg; X34 is Val, Leu, Ile, Asn or Gly; X35 is Val, Leu, Ile, Asn or Gly; X36 is Thr, Phe or Arg; X37 is Val, Leu, Ile, Asn or Gly; X38 is Val, Leu, Ile, Asn or Gly; X39 is Pro or His; X40 is Met, Ser, Gln or Cys; X41 is Val, Leu, Ile, Asn or Gly; and X42 is Met, Ser, Gln or Cys.

In another aspect, the synthetic peptide has a formula: X1-Ala-X3-X4-Thr-Cys-X7-Pro-X9-X10-X11-X12-His-Pro-X15-Thr-X17-X18-Ala-X20-Pro-X22-Trp-Val-Lys-X26-Thr-Lys-X29-X30-X31-Ala-Thr-X34-X35-X36-X37-X38-His-X40-X41-Gln (SEQ ID NO:106), wherein X1, X3, X4, X7, X11, X12, X15, X17, X18, X29, X31, X34, X35, X37, X38, and X41 are independently Val, Leu, Ile, Asn, Gly, or Glu; X9, X30, X36 are independently Thr, Phe or Arg; X10, X20, X26, and X40 are independently Met, Ser, Gln or Cys; and X22 is Pro, His, Ala or Lys.

In another aspect, the synthetic peptide has one of the following sequences:

```
GANNTCLPFQNNHPITIGACPKWVKCTKNRLATGLRNIHSIQ
LANNTCLPFQNNHPITILACPKWVKCTKNRLATGLRNIHSIQ
IAGNTCLEFQNGHPITIIACPKWVKCTKGRLATGLRNIHSIQ
NAENTCLPFQNEHPITVNACPKWVKCTKERLATGLRNIHSIQ
LAVNTCLPFQNVHPITVLACPKWVKCTKVRLATGLRNIHSIQ
LAVVTQVPTMLVPPVTVVAMPAWVKMTKVTVATVVTVNPMVQ
LAVVTCVPTMLGHPVTVVAMPAWVKSTKETVATVVTVNHMVQ
```

In another aspect, the synthetic peptide has a general formula of X1-X2-X3-X4-X5-X6-X7-X8-X9-X10-X11-X12-X13-X14-X15-X16-X17-X18-X19-X20-X21-X22 (SEQ ID NO:107), where X1 is Thr, Phe or Arg; X2 is Val, Leu, Ile, Asn or Gly; X3 is Ala or Lys; X4 is Thr, Phe or Arg; X5 is Val, Leu, Ile, Asn or Gly; X6 is Val, Leu, Ile, Asn or Gly; X7 is Thr, Phe or Arg; X8 is Val, Leu, Ile, Asn, Gly or Glu; X9 is Val, Leu, Ile, Asn or Gly; X10 is Pro or His; X11 is Met, Ser, Gln or Cys; X12 is Val, Leu, Ile, Asn or Gly; X13 is Met, Ser, Gln or Cys; X14 is Met, Ser, Gln or Cys; X15 is Thr, Phe or Arg; X16 is Val, Leu, Ile, Asn or Gly; X17 is Val, Leu, Ile, Asn or Gly; X18 is Thr, Phe or Arg; X19 is Val, Leu, Ile, Asn, Gly or Glu; X20 is Ala or Lys; X21 is Val, Leu, Ile, Asn or Gly; and X22 is Ala or Lys.

In another aspect, the synthetic peptide has a formula: Thr-Leu-Ala-X4-Ile-Ile-Thr-X8-Leu-Pro-X11-Leu-Met-X14-X15-Val-X17-X18-X19-Ala-Val-Ala (SEQ ID NO:108), wherein X4, X15 and X18 are independently Thr, Phe or Arg; X8, X17, and X19 are independently Val, Leu, Ile, Asn, Gly or Glu; and X11 and X14 are independently Met, Ser, Gln or Cys. In another aspect, the synthetic peptide has one of the following sequences:

```
TLKTIITLLPMLMMTVGTLAVA
TLAFIITELPSLMCRVGRLAVA
TLATIITVLPMLQMTNITVKVA
TVAFVVREVPSVMCRVVREAVA
```

In a particular aspect, the synthetic peptide comprises an amino acid sequence or a fragment or variant thereof capable of eliciting an immune response, e.g., neutralizing antibodies, specific to an HA protein or fragment thereof, wherein the synthetic peptide is selected from the following:

```
CDEDGVKPLILRDCCVAGWLLGNHSCDVFINVPE
CDEDGVHPLILRDCCVAIYLLGNHSCDVFILVPE
CDEDGNHPLILRDCCVAIYLLNNHSCDVFILEPL
CDEDGIHPLILRDCCVAIYLLINHSCDVFILNPG
CDLDGLHPLILRDCSVANYLLINPMCDEFILEPL
EELKKLLCRINKFEKISIIPKGSWSDHEACGVSC
EGLKHLLSRILHFIHIQIIPKNQYSDHIASGNSS
EGLKKLLCRIIKFGHISIIPKGMYSDHGACGESC
ENLKKLLCRLIKFNHISIIPKGQYSDHNACGGSC
EILKKLLCRLIKFIHISIIPKGQYSDHIACGNSC
GANNTCLPFQNNHPITIGACPKWVKCTKNRLATGLRNIHSIQ
LANNTCLPFQNNHPITILACPKWVKCTKNRLATGLRNIHSIQ
IAGNTCLEFQNGHPITIIACPKWVKCTKGRLATGLRNIHSIQ
NAENTCLPFQNEHPITVNACPKWVKCTKERLATGLRNIHSIQ
LAVNTCLPFQNVHPITVLACPKWVKCTKVRLATGLRNIHSIQ
TLKTIITLLPMLMMTVGTLAVA
TLAFIITELPSLMCRVGRLAVA
SDGDINKPLLVTDSCNKNYLLNIHSCDVTNIIEN
QDLDINKPLLNTDQMLKNYLLNIPQQDLTNIIPN
GLVAPNVMTVLPTGKVMVLPAVQYMDPGAMVIMM
GGVAHVVCTVVPITGAVCVVPAVMWMDPGASVVMS
LAVVTQVPTMLVPPVTVVAMPAWVKMTKVTVATVVTVNPMVQ
LAVVTCVPTMLGHPVTVVAMPAWVKSTKETVATVVTVNHMVQ
TLATIITVLPMLQMTNITVKVA
and
TVAFVVREVPSVMCRVVREAVA.
```

Additionally, the present invention encompasses an immunologic composition comprising a synthetic peptide as described herein, i.e., having an IS that overlaps with the IS of at least one HA protein or fragment thereof (such as HAL HA2, and/or HA3 from a human influenza virus, e.g., influenza A virus subtype H1N1, H3N2, H7N7, and/or H5N1, or HAL HA2, HA3, HA4, HA5, and/or HA9 from an avian influenza virus and/or a swine influenza virus); capable of eliciting an immune response against the HA protein or fragment thereof, e.g., neutralizing antibodies against one or more influenza viruses; having an IS that contains a frequency component of F(0.148) or F(0.145-0.149) and further contains one or more of F(0.053-0.057), F(0.074-0.079), F(0.083-0.087), F(0.160-0.168), F(0.234-0.239), F(0.280-0.286), F(0.291-0.299), and F(0.362-0.366); comprises 50 to 350 amino acids or, more preferably, 15 to 50 amino acids; and/or has a general formula or particular amino acid sequence as set forth above.

In one aspect, the synthetic peptide of the immunologic composition is suitable for use as an antigen in a vaccine. The synthetic peptide may be used alone or in combination with one or more other seasonal flu vaccine antigens. The resulting immunologic composition may provide protection against one or more flu strains.

The immunologic composition may further comprise a pharmaceutically acceptable carrier and/or excipient and/or adjuvant. Additionally, the immunologic composition may further comprise another antigen obtained from a human, swine, or avian (e.g., poultry) influenza virus, e.g., the another antigen may be obtained from one or more of influenza A virus subtypes H1, H3, H5, H7, and H9.

The present invention further envisages a method for producing the immunologic composition comprising (i) obtaining the synthetic peptide, and (ii) admixing the synthetic peptide with a pharmaceutically acceptable carrier and/or excipient and/or adjuvant.

Moreover, the invention also contemplates a synthetic peptide that (i) comprises an amino acid sequence whose informational spectrum (IS) contains a frequency component F(0.148), and (ii) produces antibodies that bind to a hemagglutinin (HA) protein of an influenza virus. The antibodies produced are preferably neutralizing antibodies. The synthetic peptide may be suitable for use as an antigen in an immunologic composition.

The present invention further encompasses a method of using at least one synthetic peptide as an immunogen in order to generate antibodies, e.g., neutralizing antibodies that specifically bind to at least one HA protein.

Additionally, the present invention contemplates an isolated nucleic acid encoding the synthetic peptide; a vector containing the nucleic acid; and an isolated cell containing the vector as well as an antibody or antigen binding fragment thereof capable of binding to the synthetic peptide.

Moreover, the invention further contemplates a therapeutic method or diagnostic method using the synthetic peptide or the antibody or antigen binding fragment thereof that binds to the synthetic peptide. For example, the synthetic peptide or the antibody or antigen binding fragment thereof that binds to the synthetic peptide are suitable for use a variety of diagnostic methods, including but not limited to, immunoassays such as ELISA, ELISPOT, enzyme multiplied immunoassay technique, radioimmunoassay, and immunofluorescence; immunoblotting assays (such as a Western blot); immunoprecipitation assays such as chromatin immunoprecipitation (ChIP), immunodiffusion, and immunoelectrophoresis; immunocytochemistry; and immunohistochemistry. These diagnostic methods (and other similar methods) involve applying the synthetic peptide or the antibody or antigen binding fragment thereof that binds to the synthetic peptide to a sample (e.g., serum or mucosal) collected from a patient believed to have the flu in order to detect and characterize the infection.

Furthermore, the present invention encompasses a method for identifying a peptide that elicits an immune response against at least one hemagglutinin (HA) protein or fragment thereof. The method comprises (1)(i) obtaining an amino acid sequence of at least one HA protein or fragment thereof; (ii) assigning an electron-ion interaction potential (EIIP) index value to each amino acid residue contained in the amino acid sequence of the HA protein or fragment; (iii) subjecting the resultant EIIP index values to discrete Fourier transformation (DFT); (iv) generating an informational spectrum (IS) of the at least one HA protein or fragment based on the EIIP index values; (2)(i) obtaining an amino acid sequence of a peptide or peptides; (ii) assigning an EIIP index value to each amino acid residue contained in the amino acid sequence of the peptide or peptides; (iii) subjecting the resultant EIIP index values to discrete Fourier transformation (DFT); (iv) generating an informational spectrum (IS) of each peptide based on the EIIP index values; (3) comparing the IS of the at least one HA protein or fragment generated in (1)(iv) to the IS of the peptide or peptides generated in (2)(iv); and (4) identifying the peptide or peptides whose IS overlap with the IS of the at least one HA protein or fragment, and based thereon identifying the peptide or peptides as one being capable of eliciting an immune response against the HA protein or fragment.

The method may further include synthesizing at least one of the identified peptides and, optionally, assessing its immunogenicity or ability to generate antibodies, preferably neutralizing antibodies, that specifically bind to said at least one HA protein. Additionally, the method may further include producing an immunologic composition comprising at least one of the identified peptides.

The HA protein or fragment thereof may be from a human influenza virus. In this instance, the HA protein or fragment thereof may be HAL HA2, and/or HA3. Alternatively, the at least one HA protein or fragment thereof may be from an avian influenza virus and/or a swine influenza virus. In this instance, the HA protein or fragment thereof is HAL HA2, HA3, HA4, HA5, and/or HA9.

A cross-spectrum (CS) based on the IS of the at least one HA protein or fragment thereof (determined using an ISM approach as described herein and generally understood in the art at the time of filing) and the IS of the synthetic peptide may contain a frequency component of F(0.148). Additionally, the IS of the synthetic peptide may comprise F(0.145-0.149) and further contain at least 1, at least 2, at least 3, at least 4, at least 5, at least 6, at least 7, or all 8 of the frequency components selected from F(0.053-0.057), F(0.074-0.079), F(0.083-0.087), F(0.160-0.168), F(0.234-0.239), F(0.280-0.286), F(0.291-0.299), and F(0.362-0.366). The at least one HA protein or fragment thereof may be HA1 from influenza A virus subtype H1N1, H3N2, H7N7, and/or H5N1 and the IS of the particular HA1 may contain F(0.236), F(0.363), F(0.285), and/or F(0.076), respectively.

The synthetic peptide may comprise 50 to 350 amino acids. More particularly, the synthetic peptide may comprise 15 to 50 amino acids.

In one aspect, the synthetic peptide has a general formula of X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34 (SEQ ID NO:102), where X1 is Met, Ser, Gln or Cys; X2 is Asp; X3 is Val, Leu, Ile, Asn, Gly or Glu; X4 is Asp; X5 is Val, Leu, Ile, Asn or Gly; X6 is Val, Leu, Ile, Asn or Gly; X7 is Pro, His, Ala or Lys; X8 is Pro or His; X9 is Val, Leu, Ile, Asn or Gly; X10 is Val, Leu, Ile, Asn or Gly; X11 is Val, Leu, Ile, Asn or Gly; X12 is Thr, Phe or Arg; X13 is Asp; X14 is Met, Ser, Gln or Cys; X15 is Met, Ser, Gln or Cys; X16 is Val, Leu, Ile, Asn or Gly; X17 is Ala or Lys; X18 is Val, Leu, Ile, Asn, Gly or Glu; X19 is Trp or Tyr; X20 is Val, Leu, Ile, Asn or Gly; X21 is Val, Leu, Ile, Asn or Gly; X22 is Val, Leu, Ile, Asn, Gly or Glu; X23 is Val, Leu, Ile, Asn or Gly; X24 is Pro or His; X25 is Met, Ser, Gln or Cys; X26 is Met, Ser, Gln or Cys; X27 is Asp; X28 is Val, Leu, Ile, Asn, Gly or Glu; X29 is Thr, Phe or Arg; X30 is Val, Leu, Ile, Asn or Gly; X31 is Val, Leu, Ile, Asn or Gly; X32 is Val, Leu, Ile, Asn, Gly or Glu; X33 is Pro or His; and X34 is Val, Leu, Ile, Asn, Gly or Glu.

In another aspect, the synthetic peptide has one of the following sequences:

```
CDEDGVKPLILRDCCVAGWLLGNHSCDVFINVPE
CDEDGVHPLILRDCCVAIYLLGNHSCDVFILVPE
CDEDGNHPLILRDCCVAIYLLNNHSCDVFILEPL
CDEDGIHPLILRDCCVAIYLLINHSCDVFILNPG
CDLDGLHPLILRDCSVANYLLINPMCDEFILEPL
SDGDINKPLLVTDSCNKNYLLNIHSCDVTNIIPN
QDLDINKPLLNTDQMLKNYLLNIPQQDLTNIIPN
```

In another aspect, the synthetic peptide has a general formula of X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34 (SEQ ID NO:103), where X1 is Gly or Glu; X2 is Val, Leu, Ile, Asn, Gly or Glu; X3 is Val, Leu, Ile, Asn or Gly; X4 is Ala or Lys; X5 is Pro, His, or Lys; X6 is Val, Leu, Ile, Asn or Gly; X7 is Val, Leu, Ile, Asn or Gly; X8 is Met, Ser, Gln or Cys; X9 is Thr, Phe or Arg; X10 is Val, Leu, Ile, Asn or Gly; X11 is Val, Leu, Ile, Asn or Gly; X12 is Pro, His, or Lys; X13 is Thr, Phe or Arg; X14 is Val, Leu, Ile, Asn, Gly or Glu; X15 is Pro, His, Ala or Lys; X16 is Val, Leu, Ile, Asn or Gly; X17 is Met, Ser, Gln or Cys; X18 is Val, Leu, Ile, Asn or Gly; X19 is Val, Leu, Ile, Asn or Gly; X20 is Pro or His; X21 is Ala or Lys; X22 is Val, Leu, Ile, Asn or Gly; X23 is Met, Ser, Gln or Cys; X24 is Trp or Tyr; X25 is Met, Ser, Gln or Cys; X26 is Asp; X27 is Pro or His; X28 is Val, Leu, Ile, Asn, Gly or Glu; X29 is Ala or Lys; X30 is Met, Ser, Gln or Cys; X31 is Val, Leu, Ile, Asn or Gly; X32 is Val, Leu, Ile, Asn, Gly or Glu; X33 is Met, Ser, Gln or Cys; and X34 is Met, Ser, Gln or Cys.

In another aspect, the synthetic peptide has one of the following sequences:

```
EELKKLLCRINKFEKISIIPKGSWSDHEACGVSC
EGLKHLLSRILHFIHIQIIPKNQYSDHIASGNSS
EGLKKLLCRIIKFGHISIIPKGMYSDHGACGESC
ENLKKLLCRLIKFNHISIIPKGQYSDHNACGGSC
EILKKLLCRLIKFIHISIIPKGQYSDHIACGNSC
GLVAPNVMTVLPTGKVMVLPAVQYMDPGAMVIMM
GGVAHVVCTVVHTGAVCVVPAVMWMDPGASVVMS
```

In yet another aspect, the synthetic peptide has a general formula of X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34-X35-X36-X37-X38-X39-X40-X41-X42 (SEQ ID NO:104), where X1 is Val, Leu, Ile, Asn or Gly; X2 is Ala or Lys; X3 is Val, Leu, Ile, Asn, Gly or Glu; X4 is Val, Leu, Ile, Asn or Gly; X5 is Thr, Phe or Arg; X6 is Met, Ser, Gln or Cys; X7 is Val, Leu, Ile, Asn or Gly; X8 is Pro or His; X9 is Thr, Phe or Arg; X10 is Met, Ser, Gln or Cys; X11 is Val, Leu, Ile, Asn or Gly; X12 is Val, Leu, Ile, Asn, Gly or Glu; X13 is Pro or His; X14 is Pro or His; X15 is Val, Leu, Ile, Asn or Gly; X16 is Thr, Phe or Arg; X17 is Val, Leu, Ile, Asn or Gly; X18 is Val, Leu, Ile, Asn or Gly; X19 is Ala or Lys; X20 is Met, Ser, Gln or Cys; X21 is Pro or His; X22 is Ala or Lys; X23 is Trp or Tyr; X24 is Val, Leu, Ile, Asn or Gly; X25 is Ala or Lys; X26 is Met, Ser, Gln or Cys; X27 is Thr, Phe or Arg; X28 is Ala or Lys; X29 is Val, Leu, Ile, Asn, Gly, or Glu; X30 is Thr, Phe or Arg; X31 is Val, Leu, Ile, Asn or Gly; X32 Ala or Lys; X33 is Thr, Phe or Arg; X34 is Val, Leu, Ile, Asn or Gly; X35 is Val, Leu, Ile, Asn or Gly; X36 is Thr, Phe or Arg; X37 is Val, Leu, Ile, Asn or Gly; X38 is Val, Leu, Ile, Asn or Gly; X39 is Pro or His; X40 is Met, Ser, Gln or Cys; X41 is Val, Leu, Ile, Asn or Gly; and X42 is Met, Ser, Gln or Cys.

In another aspect, the synthetic peptide has a formula: X1-Ala-X3-X4-Thr-Cys-X7-Pro-X9-X10-X11-X12-His-Pro-X15-Thr-X17-X18-Ala-X20-Pro-X22-Trp-Val-Lys-X26-Thr-Lys-X29-X30-X31-Ala-Thr-X34-X35-X36-X37-X38-His-X40-X41-Gln (SEQ ID NO:105), wherein X1, X3, X4, X7, X11, X12, X15, X17, X18, X29, X31, X34, X35, X37, X38, and X41 are independently Val, Leu, Ile, Asn, Gly, or Glu; X9, X30, X36 are independently Thr, Phe or Arg; X10, X20, X26, and X40 are independently Met, Ser, Gln or Cys; and X22 is Pro, His, Ala or Lys.

In another aspect, the synthetic peptide has one of the following sequences:

```
GANNTCLPFQNNHPITIGACPKWVKCTKNRLATGLRNIHSIQ
LANNTCLPFQNNHPITILACPKWVKCTKNRLATGLRNIHSIQ
IAGNTCLPFQNGHPITITACPKWVKCTKGRLATGLRNIHSIQ
NAENTCLPFQNEHPITVNACPKWVKCTKERLATGLRNIHSIQ
LAVNTCLPFQNVHPITVLACPKWVKCTKVRLATGLRNIHSIQ
LAVVTQVPTMLVPPVTVVAMPAWVKMTKVTVATVVTVNPMVQ
LAVVTCVPTMLGHPVTVVAMPAWVKSTKETVATVVTVNHMVQ
```

In another aspect, the synthetic peptide has a general formula of X1-X2-X3-X4-X5-X6-X7-X8-X9-X10-X11-X12-X13-X14-X15-X16-X17-X18-X19-X20-X21-X22 (SEQ ID NO:106), where X1 is Thr, Phe or Arg; X2 is Val, Leu, Ile, Asn or Gly; X3 is Ala or Lys; X4 is Thr, Phe or Arg; X5 is Val, Leu, Ile, Asn or Gly; X6 is Val, Leu, Ile, Asn or Gly; X7 is Thr, Phe or Arg; X8 is Val, Leu, Ile, Asn, Gly or Glu; X9 is Val, Leu, Ile, Asn or Gly; X10 is Pro or His; X11 is Met, Ser, Gln or Cys; X12 is Val, Leu, Ile, Asn or Gly; X13 is Met, Ser, Gln or Cys; X14 is Met, Ser, Gln or Cys; X15 is Thr, Phe or Arg; X16 is Val, Leu, Ile, Asn or Gly; X17 is Val, Leu, Ile, Asn or Gly; X18 is Thr, Phe or Arg; X19 is Val, Leu, Ile, Asn, Gly or Glu; X20 is Ala or Lys; X21 is Val, Leu, Ile, Asn or Gly; and X22 is Ala or Lys.

In another aspect, the synthetic peptide has a formula: Thr-Leu-Ala-X4-Ile-Ile-Thr-X8-Leu-Pro-X11-Leu-Met-X14-X15-Val-X17-X18-X19-Ala-Val-Ala (SEQ ID NO:107), wherein X4, X15 and X18 are independently Thr, Phe or Arg; X8, X17, and X19 are independently Val, Leu, Ile, Asn, Gly or Glu; and X11 and X14 are independently Met, Ser, Gln or Cys.

In another aspect, the synthetic peptide has one of the following sequences:

```
TLKTIITLLPMLMMTVGTLAVA
TLAFIITELPSLMCRVGRLAVA
```

-continued

```
TLATIITVLPMLQMTNITVKVA

TVAFVVREVPSVMCRVVREAVA
```

In a particular aspect, the synthetic peptide comprises an amino acid sequence or a fragment thereof capable of eliciting an immune response, e.g., neutralizing antibodies, specific to an HA protein or fragment thereof, wherein the synthetic peptide is selected from the following:

```
CDEDGVKPLILRDCCVAGWLLGNHSCDVFINVPE

CDEDGVHPLILRDCCVAIYLLGNHSCDVFILVPE

CDEDGNHPLILRDCCVAIYLLNNHSCDVFILEPL

CDEDGIHPLILRDCCVAIYLLINHSCDVFILNPG

CDLDGLHPLILRDCSVANYLLINPMCDEFILEPL

EELKKLLCRINKFEKISIIPKGSWSDHEACGVSC

EGLKHLLSRILHFIHIQIIPKNQYSDHIASGNSS

EGLKKLLCRIIKFGHISIIPKGMYSDHGACGESC

ENLKKLLCRLIKFNHISIIPKGQYSDHNACGGSC

EILKKLLCRLIKFIHISIIPKGQYSDHIACGNSC

GANNTCLPFQNNHPITIGACPKWVKCTKNRLATGLRNIHSIQ

LANNTCLPFQNNHPITILACPKWVKCTKNRLATGLRNIHSIQ

IAGNTCLPFQNGHPITIIACPKWVKCTKGRLATGLRNIHSIQ

NAENTCLPFQNEHPITVNACPKWVKCTKERLATGLRNIHSIQ

LAVNTCLPFQNVHPITVLACPKWVKCTKVRLATGLRNIHSIQ

TLKTIITLLPMLMMTVGTLAVA

TLAFIITELPSLMCRVGRLAVA

SDGDINKPLLVTDSCNKNYLLNIHSCDVTNIIPN

QDLDINKPLLNTDQMLKNYLLNIPQQDLTNIIPN

GLVAPNVMTVLPTGKVMVLPAVQYMDPGAMVIMM

GGVAHVVCTVVHTGAVCVVPAVMWMDPGASVVMS

LAVVTQVPTMLVPPVTVVAMPAWVKMTKVTVATVVTVNPMVQ

LAVVTCVPTMLGHPVTVVAMPAWVKSTKETVATVVTVNHMVQ

TLATIITVLPMLQMTNITVKVA
and
TVAFVVREVPSVMCRVVREAVA.
```

The peptide identified by the disclosed method may be used in the preparation of an immunologic composition, which itself may contain the peptide alone or in combination with one or more additional seasonal flu vaccine antigens. The resulting immunologic composition containing the peptide may provide protection against one or more flu strains. Accordingly, the present invention also contemplates a method for the treatment or prevention of influenza virus infection in a subject, comprising administering a therapeutically effective amount of the immunologic composition or a therapeutically effective amount of the synthetic peptide or a therapeutically effective amount of the antibody or antigen binding fragment thereof to the subject in need thereof, preferably the treated subject is a human, such that the immunologic composition or the synthetic peptide or the antibody or antigen binding fragment thereof treats or prevents influenza infection in the subject. The subject can also be a laboratory animal (e.g., mouse, rat, guinea pig, non-human primate), livestock (e.g., swine, avian), or a domestic animal (e.g., canine).

DETAILED DESCRIPTION OF THE FIGURES

FIG. 1A shows the informational spectra (IS) of HA1 from H1N1. FIG. 1B shows the IS of HA1 from H3N2. FIG. 1C shows the IS of HA1 from H7N7. FIG. 1D shows the IS of HA1 from H5N1. The abscissa represents frequencies and the ordinate represents the signal-to-noise ratio (S/N).

Figure 2:
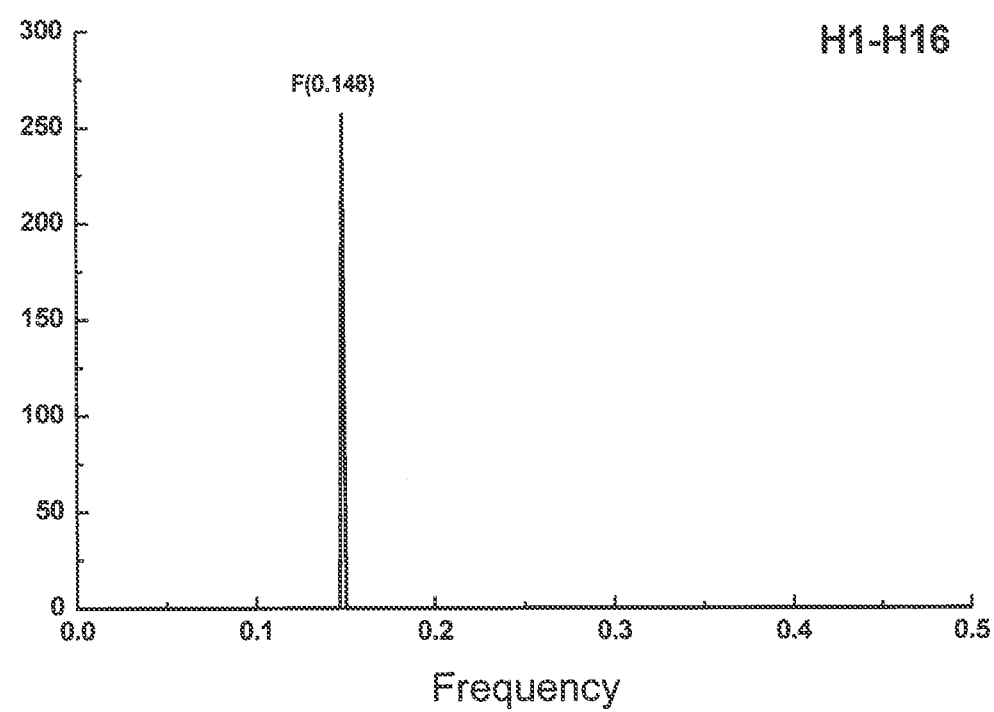

FIG. 2 shows the cross-spectrum (CS) of HA1 from all influenza virus subtypes (H1-H16). The abscissa represents frequencies and the ordinate represents the signal-to-noise ratio (S/N).

FIG. 3A shows the amino acid sequence of HA1 from influenza A/Hong Kong/213/03 (also known as H5N1 (SEQ ID NO:101)). The bolded residues within the amino acid sequence indicate the domain of HA1 that is essential for F(0.076). The essential domain comprises amino acid residues at position 42-75 within the amino acid sequence of HA1 from H5N1. FIG. 3B shows the informational spectrum (IS) of HA1 from H5N1. The abscissa represents peptide position within the H5N1 HA1 and the ordinate represents the signal-to-noise ratio (S/N).

DETAILED DESCRIPTION OF THE INVENTION

The present invention provides a novel approach to the identification of novel peptides whose EIIP structure, but not necessarily sequence, mimic conserved influenza antigenic targets and, thus, can be used to elicit an immune response against different influenza viruses. The EIIP structure refers to the electron-ion interaction potential and is unrelated to the linear amino acid sequence (primary structure) and peptide folding motifs (e.g., secondary and tertiary structure). In particular, the peptides share EIIP homology with at least one HA protein that can be derived from a human influenza virus and/or an influenza virus from an animal reservoir, such as swine or avian and, thus, can be used as an antigen (e.g., in a vaccine). As a result of the EIIP structural similarity between the identified synthetic peptide and the natural HA proteins, antibodies provided against the synthetic peptide are also capable of recognizing the natural influenza HA proteins. Accordingly, synthetic peptides whose structure mimics that of several different HA proteins, e.g., HA proteins from different influenza viruses (influenza A and influenza B, or different strains of influenza A), can be used to elicit an immune response against the several different HA proteins and, thus, provide cross-protective immunity against several different influenza viruses.

The EIIP structure that is used as the basis for peptide selection for this invention relies on the interchangeability of amino acids with similar EIIP values. Such substitutions are not the same as the substitutions traditionally described as "conserved amino acid substitutions" based on other properties (e.g., grouped by acidic, sulfur-containing, basic, or aromatic side chains). For example, based on traditional conservative substitutions, alanine may be substituted for glycine, which are both aliphatic. But according to EIIP values, these amino acids are not interchangeable because they have dissimilar EIIP value: alanine is 0.373 while glycine is And while proline (which is cyclic) and histidine (which is basic) would not be a suggested traditional conservative substitution, they are readily interchangeable according to similar EIIP values (0.0198≤EIIP≤0.242). The following chart lists the EIIP values for the amino acids:

TABLE I

EIIP VALUES FOR 20 AMINO ACIDS

| Amino acid | EIIP value |
| --- | --- |
| Leucine | 0.0000 |
| Isoleucine | 0.0000 |
| Asparagine | 0.0036 |
| Glycine | 0.0050 |
| Valine | 0.0057 |
| Glutamic acid | 0.0058 |
| Proline | 0.0198 |
| Histidine | 0.0242 |
| Lysine | 0.0371 |
| Alanine | 0.0373 |
| Tyrosine | 0.0516 |
| Tryptophan | 0.0548 |
| Glutamine | 0.0761 |
| Methionine | 0.0823 |
| Serine | 0.0829 |
| Cysteine | 0.0829 |
| Threoinine | 0.0941 |
| Phenylalanine | 0.0946 |
| Arginine | 0.0959 |
| Aspartic acid | 0.1263 |

Based EIIP similarity, the following groupings are used to designate EIIP structurally similar peptides. The group L, I, N, G, V, and E (EIIP≤0.0058) may be interchangeable with one another, and more particularly, the subgroup L, I, N, G, and V (EIIP≤0.0057) and the subgroup G and E (0.0050≤EIIP≤0.0058). The group P, H, K, and A (0.0198≤EIIP≤0.0373) may be interchangeable with one another, and more particularly the subgroup P, H, and K (0.0198≤EIIP≤0.0371), the subgroup P and H (0.0198≤EIIP≤0.242), and the subgroup K and A (0.371≤EIIP≤0.373). The group Y and W may be interchangeable (0.0516≤EIIP≤0.0548). The group Q, M, S, and C (0.0761≤EIIP≤0.0829) may be interchangeable. The group T, F, and R (0.0941≤EIIP≤0.0959) may be interchangeable. In general, D (EIIP=0.1263) is not interchangeable with other amino acids.

Influenza is a global health concern, with the annual attack rate estimated at 5%-10% in adults and 20%-30% in children. Given its disease-causing potential, the prevention of infection with influenza viruses is a high public health priority. Currently, the most effective single way of protecting people against influenza infection and disease is vaccination. The influenza virus belongs to the family Orthomyxoviridae and is divided into the A, B and C genera, which are distinguishable on the basis of antigenic differences between their matrix and nucleoproteins, their host range, variations in surface glycoproteins, genome organization, and morphology. Within the influenza virus genera, influenza A and B viruses are the most relevant clinically because they cause severe respiratory infections in humans. Of the two, type A viruses are more virulent, cause the most severe disease and are the primary pathogens responsible for seasonal and pandemic influenza outbreaks.

Type A viruses can be divided into different subtypes based on the serotypes of their main surface antigens: hemagglutinin (HA) and neuraminidase (NA). Phylogenetically, HA subtypes are categorized into two groups (H1, H2, H5, H6, H8, H9, H11, H12, H13, H16, H17, and H18 in group 1, and H3, H4, H7, H10, H14, and H15 in group 2). Historically, H1 (H1N1), H2 (H2N2) and H3 (H3N2) strains have caused influenza pandemics in humans and resulted in millions of deaths.

Influenza B viruses have diverged into two antigenically and phylogenetically distinct lineages that co-circulate in the environment. Infections caused by influenza B viruses are less severe, but the pathogen can still cause outbreaks. The influenza C virus is of little concern for human infections, causing only a mild common cold-like disease in children.

The invention generally relates to the development of a universal influenza vaccine capable of providing broad protection against different strains of the flu. More particularly, the invention related to the use of an information spectrum method (ISM) to identify novel peptides sharing structural homology with hemagglutinin (HA) from different influenza A and/or influenza B subtypes, and vaccines comprising the HA multi-epitope peptide antigen that is capable of eliciting cross-protective immunity against several different influenza A and/or influenza B subtypes. The universal flu vaccine can be used alone or in combination with strain-specific seasonal flu vaccines.

Currently available vaccines against influenza are generally poorly immunogenic and do not induce long-lasting serum antibody titers. These vaccines provide protection only against a subset of strains circulating in the environment, namely, those closely related to the vaccine strains. This limited effectiveness is due to a mechanism called "antigenic drift", in which the influenza virus undergoes genetic variations that allow it to evade the pre-existing immune responses of the host. Therefore, immune responses mounted against earlier forms of the virus are less effective or completely ineffective against newer variants. As a result, a new vaccine must be reformulated and prepared every flu season.

The vaccine has to be based on a surveillance of antigenic drift and predictions of the dominant strain for the upcoming flu season. The strains are selected by a network of experts several months in advance before the next influenza season regarding the duration of the manufacturing process. Although the process of antigenic drift is well studied, precise predictions of what strains will circulate in a given season remains problematic. Mismatches between vaccine strains and circulating viruses occur, resulting in a sharp drop in vaccine efficacy. Moreover, current vaccines appear to be less effective in the elderly. Of note, currently available vaccines do not protect against possible pandemics resulting from genetic variations between different subtypes of the influenza virus concurrently infecting the same host. Additionally, it takes at least 6-8 months to develop, test and produce conventional vaccines against emerging viruses. The reformulation of the annual flu vaccine is also an expensive undertaking that costs consumers and the global health system more than $4 billion each year.

The efficacy rate of influenza vaccines available in the U.S. is approximately 59% for adults. Yet, vaccine effectiveness against H3N2, the main flu strain circulating during the 2012-2013 season, proved to be only 46% for adults aged 18-49, 50% for those aged 50-64, and a dismal 9% for people aged over 65, who represent a vulnerable group. The low effectiveness of currently available flu vaccines results, among other reasons, from the low use of the seasonal influenza vaccine. This is caused by the necessity of yearly vaccine readministration, related cost issues, lack of influenza vaccine acceptance in the general population, and unknown efficacy for a given season. Sensational media coverage and public debate concerning vaccine effectiveness, which depends on the match between the circulating virus and the vaccine strains, can negatively impact vaccination coverage. Another growing problem is the public attitude to the adjuvants present in vaccines. Thus, in the event of a pandemic, vaccination could be ineffective. To overcome the limitations of seasonal influenza virus vaccines and enhance our pandemic preparedness, it is desirable to develop a vaccine that provides universal and durable protection.

The development of universal vaccines relies, in large part, on the utilization of highly conserved antigenic targets. However, conserved antigen epitopes are usually less exposed to the host immune system, and as such, are more weakly immunogenic.

Several proteins encoded by the influenza virus have been evaluated as promising candidate antigens for the development of a universal vaccine. Among them are the HA, M (M1 and M2e), NP, and NA proteins, all of which have highly conserved regions that are potential immunogens for a universal vaccine.

HA, the major envelope glycoprotein of influenza A viruses, is the target of almost all neutralizing antibodies. HA is synthesized as an immature polypeptide chain called HA0, which is activated upon cleavage by host proteases to yield two subunits, HA1 and HA2. HA2 creates a helical chain "stem" that is anchored in the viral lipid membrane. The HA1 subunit of HA forms a globular "head" that contains receptor binding sites and the majority of the virus antigenic sites. Because HA1 loops are highly variable, antibodies targeting these regions are strain-specific, explaining why immunity by natural exposure or vaccination is typically restricted to the currently circulating strains. It has been estimated that human seasonal H3 and H1 viruses have undergone between 2.1% and 3% amino acid changes per drift variant between 1999 and 2010. In contrast to HA1, the HA2 subunit is highly conserved among viruses belonging to the same phylogenic group. It also undergoes mutations, but at a much lower rate, e.g., it underwent only 3 different amino acid changes in this region in the H1 and H3 strains in the same period of time. Furthermore, HA2 is also immunogenic.

The first report describing an antibody cross-reactive with the HA stem was published almost 20 years ago (Okuno et al., 1993 *J. Virol.* 67(5):2552-8). The mouse antibody C179 neutralizes the H1, H2, H5, H6, and H9 subtypes of the virus (Okuno et al., 1993; Sakabe et al., 2010 *Antiviral Res.* 88(3): 249-255; Smirnov et al., 1999 *Acta Virol.* 43(4):237-44) and, subsequently, human antibodies capable of neutralizing many different subtypes of the influenza virus were also identified, e.g., CR 6261 and F10) (Sui et al., 2009 *Nat Struct Mol Biol.* 16(3):265-73; Throsby et al., 2008 *PLoS One* 3(12): e3942; Kashyap et al., 2008 *PNAS* 105(16): 5986-91; Ekiert et al., 2009 *Science* 324(5924):246-51; CR8020 and CR8043 (Ekiert et al., 2011 *Science* 333(6044): 843-50; Friesen et al., 2014 *PNAS* 111(1): 445-450); and F16 (Corti et al., 2011 *Science* 333(6044): 850-856; Russell, 2011 NEJM 365:1541-1542; Clementi et al., 2011 *PLoS One* 6(12): e28001). Similarly, antibodies (CR8033 and CR8071) were identified as recognizing conserved epitopes in the HA head region of influenza B (Dreyfus et al., 2012 *Science* 337(6100):1343-1348). Furthermore, an antibody (CR9114) that recognizes epitopes in the HA stem of both influenza A and influenza B, and which protects against lethal challenges from both of these genera, was discovered (Dreyfus et al., 2012, Id.). CR9114 is the most broadly neutralizing antibody identified to date. In addition to cross-reacting antibodies that bind to the conserved regions of HA2, broadly neutralizing antibodies (bnAbs) that recognize regions on HA1 were also identified (Ohshima et al., 2011 *J Virol* 85:11048-11057; Ekiert et al., 2012 *Nature* 489(7417):526-32; Tsibane et al., 2012 *PLoS Pathog.* 8(12): e1003067). Such broadly cross-reactive HA stem antibodies may provide protection through passive transfer (Ekiert et al., 2011; Corti et al., 2010 *J Clin Invest.* 120(5):1663-73; Sui et al., 2009; Corti et al., 2013 *Annu Rev Immunol* 31: 705-742).

The identification of bnAbs against influenza viruses raised hopes for the development of the universal vaccines for influenza. There have been some attempts to use full length HA to elicit a broad neutralizing response, but it is challenging to induce immunological responses to conserved regions that are weakly immunogenic. Indeed, at least in some reports, the bnAbs did not neutralize the influenza virus (Schneemann et al., 2012 *J Virol.* 86(21): 11686-11697). For those bnAbs that may provide protection against homologous challenges, the immunological response is weak and, thus, it may be necessary to preimmunize before vaccination with a vaccine based on these bnAbs. Additionally, the safety of influenza vaccines based on HA stem domain antigens is questionable. Recent studies demonstrated that elicited non-neutralizing anti-stalk antibodies might promote infection by enhancing virus membrane fusion activity (To et al., 2012 *Clin Vaccine Immunol* 19(7):1012-1018).

Therefore, it is desirable to develop a novel approach to the identification of novel antigens having conserved homology with HA from different influenza virus and, thus, capable of eliciting cross-protective immunity against different flu strains.

The present invention uses an ISM approach, rather than traditional neutralization assays, to identify structural characteristics of influenza peptides and, based thereon, obtain novel peptide antigens having a spectral profile overlapping, at least in part, with the spectral profile of the influenza peptide(s). The broad neutralization capacity against different subtypes of influenza virus (H1-H18), combined with the flexibility in the primary structure of the identified novel antigen(s) (i.e., the peptide(s) share structural homology, but not necessarily a linear amino acid sequence, with the influenza peptide(s)), provide broad protectivity across flu strains and, thus, provide a universal flu vaccine.

Accordingly, these peptides as well as the immunologic compositions comprising them can be used individually, in combination with one another, or in combination with seasonal flu vaccine antigens. For the influenza strains expected to be the most common that year, based on traditional research approaches, the strain-specific antigens may confer the best protection. However, the universal flu peptide provides an extra layer of protection for strains that were not predicted for this year, e.g., due to antigenic drift and/or antigenic shift, and in instances where the seasonal flu vaccine is poorly matched to the circulating influenza viruses.

In the ISM approach, sequences (protein or nucleotide) are transformed into signals by assigning a numerical value to each element (amino acid or nucleotide). These values correspond to the electron-ion interaction potential (EIIP), which determines electronic properties of amino acids and nucleotides. The signal obtained is then decomposed into a periodical function by Fourier transformation, resulting in a series of frequencies (F) and their amplitudes (A). The obtained frequencies correspond to the distribution of structural motifs with defined physico-chemical characteristics that are responsible for the biological function of the sequence. In other words, the peak frequencies of IS of a protein sequence reflect its biological or biochemical functions. See Veljkovic et al., *Current Medicinal Chemistry* (2007) 14:133-135, which is herein incorporated by reference in its entirety.

When comparing proteins that share the same biological or biochemical function(s), this technique allows the detection of code/frequency pairs that are specific for their common biological properties. The method is insensitive to the location of the motifs and, thus, does not require previous alignment of the sequences.

More particularly, it is generally believed that the number of valence electrons and the EIIP representing the main energy term of valence electrons are essential physical parameters determining the long-range properties of biological molecules. EIIP for organic molecules can be determined by the following simple equation derived from the "general model pseudopotential":

$$W=0.25Z^*\sin(1.04pZ^*)/2\pi$$

where $Z^*$ is the average quasivalence number (AQVN) determined by $$Z^*=\Sigma^m n_i Z_i/N$$

And wherein $Z_i$ is the valence number of the i-th atomic component, $n_i$ is the number of atoms of the i-th component, m is the number of atomic components in the molecule, and N is the total number of atoms. The EIIP values calculated according to equations (1) and (2) are in Rydbergs (Ry). The strong connection between EIIP and AQVN of organic molecules and their biological activity has previously demonstrated, e.g., in the context of mutagenicity, carcinogenicity, toxicity, antibiotic activity, and cytostatic activity.

A sequence of N residues is represented as a linear array of N terms, with each term given a weight. The weight assigned to a residue is EIIP, determining electronic properties of amino acids and nucleotides, which are responsible for their intermolecular interactions. In this way the alphabetic code of protein or nucleotide sequence is transformed into a sequence of numbers. The obtained numerical sequence, representing the primary structure of protein, is then subjected to a discrete Fourier transformation, which is defined as follows:

$$X(n)=\Sigma x(m)e^{-j(2/N)nm}, n\text{ is }1,2,\ldots,N/2$$

Where x(m) is the m-th member of a given numerical series, N is the total number of points in this series, and X(n) are discrete Fourier transformation coefficients. These coefficients describe the amplitude, phase and frequency of sinusoids, which comprise the original signal. The absolute value of complex discrete Fourier transformation defines the amplitude spectrum and the phase spectrum. The complete information about the original sequence is contained in both spectral functions.

In this way, sequences are analyzed as discrete signals. It is assumed that their points are equidistant with the distance d is 1. The maximal frequency in a spectrum defined in this way is F is 1/2d is 0.5. The frequency range is independent of the total number of points in the sequence. The total number of points in a sequence influences only the resolution of the spectrum. The resolution of the N-point sequence is 1/n. The n-th point in the spectral function corresponds to a frequency f(n) is of is n/N. Thus, the initial information defined by the sequence of amino acids can now be presented in the form of the informational spectrum (IS), representing the series of frequencies and their amplitudes. The IS frequencies correspond to distribution of structural motifs with defined physicochemical properties determining a biological function of a protein. When comparing proteins, which share the same biological or biochemical function, the ISM technique allows detection of code/frequency pairs which are specific for their common biological properties, or which correlate with their specific interaction. This common informational characteristic of sequences is determined by a cross-spectrum (CS). A CS of N spectra is obtained by the following equation:

$$C(j)=\pi S(i,j)$$

where $\pi(i,j)$ is the j-th element of the i-th power spectrum and C(j) is the j-th element of CS.

Thus, CS is the Fourier transform of the correlation function for the spectrum. In this way, any spectral component (frequency) not present in all compared informational spectra is eliminated. Peak frequencies in CS are common frequency components for the analyzed sequences. A measure of similarity for each peak is the signal-to-noise ratio (S/N), which represents a ratio between signal intensity at one particular IS frequency and the main value of the whole spectrum. If one calculates the CS for a group of proteins, which have different primary structures, and finds strictly defined peak frequencies, it means that primary structures of the analyzed proteins encode the same information. It was demonstrated that: 1) such a peak exists only for the group of proteins with the same biological function; 2) no significant peak exists for biologically unrelated proteins; 3) peak frequencies are different for different biological functions. Furthermore, it was shown that the proteins and their targets (ligand/receptor, antibody/antigen, etc.) have the same characteristic frequency(ies) in common. Thus, it can be postulated that IS frequencies characterize not only the general function but also recognition and interaction between a particular protein and its target. Once the characteristic frequency for a particular protein function/interaction is identified, it is possible then to utilize the ISM approach to predict the amino acids in the sequence, which essentially contribute to this frequency and are likely to be crucial for the observed function.

The calculation of the IS and CS of HA amino acid sequences from different flu strains (H1-H18) allowed the identification of conserved domains, e.g., structural properties, that likely play a role in the interaction of the viral HA protein with the cellular receptor.

The entry of influenza virus into susceptible cells is mediated by the viral HA membrane glycoprotein, which binds sialic acids of cell-surface glycoproteins and glycolipids. The binding preference of a given HA for different receptors correlates to some extent with the species specificity for infection. For example, human isolates preferentially bind to receptors with α2,6 linkages to galactose (SAα2,6Gal), whereas avian isolates prefer α2,3 linkages (SAα2,3Gal). A change in receptor preference is, however, not necessary since the lower respiratory tract also expresses a 2,3 receptors. It has also been reported that influenza virus can infect host cells via a sialic acid-independent pathway, either directly or in a multistage process. It has been speculated that sialic acid enhances virus binding to secondary receptors that mediate entry.

Several approaches, such as structural analyses, model protein evolution, and mathematical modeling have been taken to study the antigenic drift and shift of influenza A viruses. All of these approaches trace changes in HA, but they do not allow precise assessment of biological consequences. In the present invention, ISM was applied to identify the spectral properties of HA proteins from individual flu strains and, further, to identify shared spectral properties of the different HA proteins such that a "common epitope" was identified.

Using this information, the inventors have identified synthetic peptides that differ in amino acid sequence from the naturally-occurring influenza peptides but possess the same or similar structural features as the viral protein(s) that are important for interacting with the host cell. As such, these synthetic peptides can be used as a novel influenza antigen(s), e.g., capable of eliciting an immune response against the HA protein or fragment thereof, e.g., suitable for use as an antigen to produce antibodies (preferably, neutralizing antibodies) that bind to the at least one HA protein or fragment thereof. Additionally, because the synthetic peptides contain structural features that shared among viral HA proteins from different flu strains, the synthetic peptides effectively possess a multi-epitope that may be capable of eliciting immunity against several different influenza subtypes and, thus, provide cross-protective or universal immunity.

The synthetic peptides of the present invention can be administered by different methods, e.g., topically, intranasally, or through parenteral administration, such as through subcutaneous injection, intra-muscular injection, intravenous injection, intraperitoneal injection, or intradermal injection, to a subject in need thereof, e.g., humans, horses, swine, canine and other mammals or avians, etc. The peptides can be used individually or in combination. Additionally, the peptide may be administered alone or as part of a composition that further comprises one or more pharmaceutically acceptable carriers, the proportion of which is determined by the solubility and chemical nature of the peptide, chosen route of administration and standard biological administration. Because inventive peptides may target proteins on the surfaces of the virus and/or the cell, to ensure efficacy, the carrier in such formulations optionally are free or substantially free (e.g., at least 90, 95, 98, or 99 wt %) of proteins that bind to the peptides.

Suitable pharmaceutically acceptable carriers for the compositions containing the peptides are described in the standard pharmaceutical texts. See, e.g., *Remington's Pharmaceutical Sciences*, $18^{th}$ Ed., Mack Publishing Company, Easton, Pa. (1990). Specific non-limiting examples of suitable pharmaceutically acceptable carriers include water, saline, dextrose, glycerol, ethanol, or the like and combinations thereof. In addition, if desired, the composition can further contain minor amounts of auxiliary substances such as wetting or emulsifying agents, pH buffering agents that enhance the antiviral effectiveness of the composition.

Depending on the route of administration, the composition may take the form of a solution, suspension, tablet, pill, capsule, sustained release formulation, powder, cream, lotion, emulsion, or the like.

For topical administration, the antiviral peptide can be formulated into a composition containing an effective amount of the antiviral peptide, typically 0.01 or 0.1 to 10%, of the peptide. Such compositions are typically in the form of a solution, cream, lotion, or emulsion.

For parenteral administration, the peptides of the present disclosure may be administered by intravenous, subcutaneous, intramuscular, intraperitoneal, or intradermal injection, alone or in compositions further comprising pharmaceutically accepted carriers. For administration by injection, it is preferred to use the antiviral peptide in a solution in a sterile aqueous vehicle which may also contain other solutes such as buffers or preservatives as well as sufficient quantities of pharmaceutically acceptable salts or of glucose to make the solution isotonic. The antiviral peptides of the present disclosure can be obtained in the form of therapeutically acceptable salts that are well-known in the art.

The antiviral peptides of the present disclosure may be used for treating viral infections of the respiratory tract. Thus, in one embodiment, the antiviral peptides can also be delivered locally to the respiratory system, for example to the nose, sinus cavities, sinus membranes or lungs. The peptide(s), or pharmaceutical compositions containing one or more peptides, can be delivered to the respiratory system in any suitable manner, such as by inhalation via the mouth or intranasally. The present compositions can be dispensed as a powdered or liquid nasal spray, suspension, nose drops, a gel or ointment, through a tube or catheter, by syringe, by packtail, by pledget, or by submucosal infusion. The peptides may be conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the peptide and a suitable powder base such as lactose or starch. Examples of intranasal formulations and methods of administration can be found in PCT publications WO 01/41782, WO 00/33813, and U.S. Pat. Nos. 6,180,603; 6,313,093; and 5,624,898. The latter-cited U.S. patents are incorporated herein by reference and for all purposes. A propellant for an aerosol formulation may include compressed air, nitrogen, carbon dioxide, or a hydrocarbon based low boiling solvent. The peptide or peptides of the present disclosure can be conveniently delivered in the form of an aerosol spray presentation from a nebulizer or the like. In some aspects, the active ingredients (i.e., peptides) are suitably micronized so as to permit inhalation of substantially all of the active ingredients into the lungs upon administration of the dry powder formulation, thus the active ingredients will have a particle size of less than 100 microns, desirably less than 20 microns, and preferably in the range 1 to 10 microns. In one embodiment, one or more of the antiviral peptides are packaged into a device that can deliver a predetermined, and generally effective, amount of the peptide via inhalation, for example a nasal spray or inhaler.

The optimal concentration of the peptide or peptides will necessarily depend upon the specific peptide(s) used, the characteristics of the patient, and the nature or particular type of the influenza virus. These factors can be determined by those of skill in the medical and pharmaceutical arts in view of the present disclosure. In general, the peptides are most desirably administered at a concentration level that will generally afford antiviral effective results against the selected virus(es) without causing any harmful or deleterious side effects. Specific dosages may be adjusted depending on conditions of disease, the age, body weight, general health conditions, sex, diet of the subject, dose intervals, administration routes, excretion rate, and combinations of drugs. Any of the above dosage forms containing effective amounts are well within the bounds of routine experimentation and therefore, well within the scope of the instant disclosure. A therapeutically effective dose may vary depending upon the route of administration and dosage form.

It will be further appreciated that the amount of an antiviral peptide of the present disclosure that is useful will vary not only with the particular peptide selected but also with the route of administration, and the age and condition of the patient, and will ultimately be at the discretion of the attendant physician or veterinarian. In general however, a suitable dose will be in the range of from about 0.01 to 750 mg/kg of body weight per day preferably in the range of 0.1 to 100 mg/kg/day, most preferably in the range of 0.5 to 25 mg/kg/day.

The peptides of the present disclosure may be administered therapeutically or prophylactically. Treatment is preferably commenced before or at the time of infection or at the time the mammal is exposed to a virus that is capable of causing a viral respiratory infection, and continued until virus is no longer present or active in the respiratory tract. However, the treatment can also be commenced post-infection, after the mammal has been exposed to a virus that is capable of causing a viral respiratory infection, or after the appearance of established symptoms of infection.

Suitable treatment is given 1-4 times daily and continued for 1-10 days, and typically 8 days post infection. Suitable prophylactic administration is given in single or multiple doses that may be spaced apart in accordance with known booster vaccination schedules and/or given annually in accordance with current influenza vaccination schedules.

The desired dose may be presented in a single dose or as divided doses administered at appropriate intervals, for example as two, three, four or more sub-doses per day.

The peptide may be conveniently administered in unit dosage form, for example, containing 10 to 1500 mg, conveniently 20 to 1000 mg, most conveniently 50 to 700 mg of active ingredient per unit dosage form, e.g. 1 mg/kg equates to 75 mg/75 kg of body weight.

The present peptides can also be provided as pharmaceutically acceptable salts. A "pharmaceutically acceptable salt" includes a salt with an inorganic base, organic base, inorganic acid, organic acid, basic amino acid, or acidic amino acid. As salts of inorganic bases, the disclosure includes, for example, alkali metals such as sodium or potassium; alkaline earth metals such as calcium and magnesium or aluminum; and ammonia. As salts of organic bases, the disclosure includes, for example, trimethylamine, triethylamine, pyridine, picoline, ethanolamine, diethanolamine, and triethanolamine. As salts of inorganic acids, the instant disclosure includes, for example, hydrochloric acid, hydroboric acid, nitric acid, sulfuric acid, and phosphoric acid. As salts of organic acids, the instant disclosure includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant disclosure includes, for example, arginine, lysine and ornithine. Acidic amino acids include, for example, aspartic acid and glutamic acid.

The following examples are offered to illustrate, but not to limit, the claimed invention.

EXAMPLES

Example 1: Analysis of Amino Acid Sequences Using the Informational Spectrum Method (ISM)

ISM is based on the premise that the protein-protein interaction encompasses two basic steps: (i) recognition and targeting between interacting proteins (long-range interactions at distances >100 Å) and (ii) chemical binding (short range interactions at distances <5 Å). The long-range properties of biological molecules are determined by the electron-ion interaction potential (EIIP) representing the main energy term of valence electrons. The EIIP for organic molecules can be calculated by the following simple equation derived from the "general model pseudopotential":

$$W = 0.25 Z^* \sin(1.04\pi Z^*)/2\pi \quad (1)$$

where $Z^*$ is the average quasivalence number (AQVN) determined by $$Z^* = \Sigma^m n_i Z_i / N \quad (2)$$

where $Z_i$ is the valence number of the i-th atomic component, $n_i$ is the number of atoms of the i-th component, m is the number of atomic components in the molecule, and N is the total number of atoms.

Applying the given expressions (1) and (2) to 20 amino acids, the following EIIP values are obtained (in Ry): L 0.0000, I 0.0000, N 0.0036, G 0.0050, V 0.0057, E 0.0058, P 0.0198, H 0.0242, K 0.0371, A 0.0373, Y 0.0516, W 0.0548, Q 0.0761, M 0.0823, S 0.0829, C 0.0829, T 0.0941, F 0.0946, R 0.0959 and D 0.1263. The ISM technique is based on a model of the primary structure of a protein using a sequence of numbers, by assigning to each amino acid the correspondence value of EIIP. The obtained numerical sequence, representing primary structure of protein, is then subjected to a discrete Fourier transformation which is defined as follows:

$$X(n) = \Sigma x(m) e^{-j(2\pi/N)nm}, \ n \text{ is } 1,2,\ldots,N/2 \quad (3)$$

where x(m) is the m-th member of a given numerical series, N is the total number of points in this series, and X(n) are discrete Fourier transformation coefficients.

These coefficients describe the amplitude, phase and frequency of sinusoids, which comprised the original signal. The absolute value of a complex discrete Fourier transformation defines the amplitude spectrum and the phase spectrum. The complete information about the original sequence is contained in both spectral functions. However, in the case of protein analysis, relevant information is presented in an energy density spectrum, which is defined as follows:

$$S(n) = X(n) X^*(n) \text{ is } |X(n)|^2, \ n \text{ is } 1,2,\ldots,N/2. \quad (4)$$

In this way, sequences are analyzed as discrete signals. It is assumed that their points are equidistant with the distance d is 1. The maximal frequency in a spectrum defined as above is F is 1/2d is 0.5. The frequency range is independent of the total number of points in the sequence. The total number of points in a sequence influences only the resolution of the spectrum. The resolution of the N-point sequence is 1/n. The n-th point in the spectral function corresponds to a frequency f(n) is of is n/N. Thus, the initial information defined by the sequence of amino acids can now be presented in the form of the informational spectrum (IS), representing the series of frequencies and their amplitudes.

The IS frequencies correspond to the distribution of structural motifs with defined physicochemical properties determining a biological function of a protein. When comparing proteins, which share the same biological or biochemical function, the ISM technique allows detection of code/frequency pairs which are specific for their common biological properties, or which correlate with their specific interaction. These common informational characteristics of sequences are determined by cross-spectrum or consensus informational spectrum (CIS). A CIS of N spectra is obtained by the following equation:

$$C(j) = \Pi S(i,j) \quad (5)$$

where H(i,j) is the j-th element of the i-th power spectrum and C(j) is the j-th element of CIS.

Thus, CIS is the Fourier transform of the correlation function for the spectrum. Thus, any spectral component (frequency) not present in all compared informational spectra is eliminated. Peak frequencies in CIS represent the common information encoded in the primary structure of analyzed sequences. This information corresponds to the mutual long-range interaction between analyzed proteins or their interaction with the common interactor.

ISM analysis provides the ability to: (i) predict the biological function of protein; (ii) compare the biological activity within a group of proteins with the same function; (iii) predict mutations which could increase or decrease biological activity of protein; and (iv) design an artificial protein sequence with desired biological function.

Example 2: Use of ISM to Analyze HA1 from Influenza a Viruses

The analysis comprised the following steps:
1. each amino acid sequence was converted to the numerical sequence by representing each amino acid with the corresponding value of the EIIP;
2. this numerical sequence was converted into a numerical spectrum using fast Fourier transform (FFT); and
3. spectra were mutually compared using cross-spectral analysis with the aim to extract common frequency components.

From the ISM analysis of HA1 molecules from various subtypes influenza A viruses (see FIG. 1), the frequencies F(0.236), F(0.363), F(0.285) and F(0.076) were identified as spectral characteristics of H1N1, H3N2, H7N7, and H5N1, respectively. F(0.148) was identified as the common frequency component in the cross-spectrum generated from the IS of the HA1 from each influenza A virus subtype (H1-H16) (see FIG. 2).

Example 3: Use of ISM to Identify the Region of H5N1 HA1 with Essential Contribution to the IS Frequency F(0.076)

The computer-assisted scanning of the domain essential for the common spectral characteristic F(0.076) of HA1 from A/Hong Kong/213/03 (H5N1) was performed as described in Example 1. The results are shown in FIG. 3. According to the analysis, the domain encompassing residues 42-75 of H5N1 HA1 provides the principal contribution to F(0.076) identified in the IS.

The examples given above are merely illustrative and are not meant to be an exhaustive list of all possible embodiments, applications, or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, the various modifications of the described modes of carrying out the invention, which are apparent to those skilled in the relevant fields, are intended to be within the scope of the appended claims.

What is claimed is:

1. An isolated synthetic peptide or an immunologic composition comprising said synthetic peptide wherein said synthetic peptide has an informational spectrum (IS) that overlaps with the IS of at least one hemagglutinin (HA) protein or fragment thereof, wherein the synthetic peptide is capable of eliciting an immune response against the HA protein or fragment thereof, wherein the synthetic peptide comprises an amino acid sequence selected from:

```
CDEDGVKPLILRDCCVAGWLLGNHSCDVFINVPE

CDEDGVHPLILRDCCVAIYLLGNHSCDVFILVPE

CDEDGNHPLILRDCCVAIYLLNNHSCDVFILEPL

CDEDGIHPLILRDCCVAIYLLINHSCDVFILNPG

CDLDGLHPLILRDCSVANYLLINPMCDEFILEPL

EELKKLLCRINKFEKISIIPKGSWSDHEACGVSC

EGLKHLLSRILHFIHIQIIPKNQYSDHIASGNSS

EGLKKLLCRIIKFGHISIIPKGMYSDHGACGESC

ENLKKLLCRLIKFNHISIIPKGQYSDHNACGGSC

EILKKLLCRLIKFIHISIIPKGQYSDHIACGNSC

GANNTCLPFQNNHPITIGACPKWVKCTKNRLATGLRNIHSIQ

LANNTCLPFQNNHPITILACPKWVKCTKNRLATGLRNIHSIQ

IAGNTCLPFQNGHPITIIACPKWVKCTKGRLATGLRNIHSIQ

NAENTCLPFQNEHPITVNACPKWVKCTKERLATGLRNIHSIQ

LAVNTCLPFQNVHPITVLACPKWVKCTKVRLATGLRNIHSIQ

TLKTIITLLPMLMMTVGTLAVA

TLAFIITELPSLMCRVGRLAVA

SDGDINKPLLVTDSCNKNYLLNIHSCDVTNIIPN

QDLDINKPLLNTDQMLKNYLLNIPQQDLTNIIPN

GLVAPNVMTVLPTGKVMVLPAVQYMDPGAMVIMM

GGVAHVVCTVVHTGAVCVVPAVMWMDPGASVVMS

LAVVTQVPTMLVPPVTVVAMPAWVKMTKVTVATVVTVNPMVQ

LAVVTCVPTMLGHPVTVVAMPAWVKSTKETVATVVTVNHMVQ

TLATIITVLPMLQMTNITVKVA

TVAFVVREVPSVMCRVVREAVA.
```

2. The isolated synthetic peptide or immunologic composition according to claim 1, wherein:
    (i) the synthetic peptide is an antigen in a vaccine;
    (ii) the synthetic peptide according to any of the foregoing alone or in combination with one or more seasonal flu vaccine antigens;
    (iii) the synthetic peptide according to any of the foregoing alone or in combination with one or more seasonal flu vaccine antigens;
    (iv) the immunologic composition according to any of the foregoing provides protection against one or more flu strains;
    (v) the immunologic composition according to any of the foregoing further comprises a pharmaceutically acceptable carrier and/or excipient and/or adjuvant;
    (vi) the immunologic composition according to any of the foregoing further comprises another antigen obtained from a human or poultry influenza virus; optionally obtained from one or more of influenza A virus subtype H1, H3, H5, H7, and H9; or
    (vii) the immunologic composition comprises any combination of the foregoing.

3. An isolated synthetic peptide that (i) comprises an amino acid sequence whose informational spectrum (IS) contains a frequency component F(0.148), and (ii) induces antibodies that bind to a hemagglutinin (HA) protein of an influenza virus, wherein the synthetic peptide comprises an amino acid sequence selected from:

```
CDEDGVKPLILRDCCVAGWLLGNHSCDVFINVPE

CDEDGVHPLILRDCCVAIYLLGNHSCDVFILVPE

CDEDGNHPLILRDCCVAIYLLNNHSCDVFILEPL

CDEDGIHPLILRDCCVAIYLLINHSCDVFILNPG

CDLDGLHPLILRDCSVANYLLINPMCDEFILEPL

EELKKLLCRINKFEKISIIPKGSWSDHEACGVSC

EGLKHLLSRILHFIHIQIIPKNQYSDHIASGNSS

EGLKKLLCRIIKFGHISIIPKGMYSDHGACGESC

ENLKKLLCRLIKFNHISIIPKGQYSDHNACGGSC

EILKKLLCRLIKFIHISIIPKGQYSDHIACGNSC

GANNTCLPFQNNHPITIGACPKWVKCTKNRLATGLRNIHSIQ

LANNTCLPFQNNHPITILACPKWVKCTKNRLATGLRNIHSIQ

IAGNTCLPFQNGHPITIIACPKWVKCTKGRLATGLRNIHSIQ

NAENTCLPFQNEHPITVNACPKWVKCTKERLATGLRNIHSIQ

LAVNTCLPFQNVHPITVLACPKWVKCTKVRLATGLRNIHSIQ

TLKTIITLLPMLMMTVGTLAVA

TLAFIITELPSLMCRVGRLAVA

SDGDINKPLLVTDSCNKNYLLNIHSCDVTNIIPN

QDLDINKPLLNTDQMLKNYLLNIPQQDLTNIIPN

GLVAPNVMTVLPTGKVMVLPAVQYMDPGAMVIMM

GGVAHVVCTVVHTGAVCVVPAVMWMDPGASVVMS

LAVVTQVPTMLVPPVTVVAMPAWVKMTKVTVATVVTVNPMVQ

LAVVTCVPTMLGHPVTVVAMPAWVKSTKETVATVVTVNHMVQ

TLATIITVLPMLQMTNITVKVA
and

TVAFVVREVPSVMCRVVREAVA.
```

4. A method for identifying a peptide that elicits an immune response against at least one hemagglutinin (HA) protein or fragment thereof according to claim 1, comprising the following:
    (1)(i) obtaining an amino acid sequence of at least one HA protein or fragment thereof; (ii) assigning an electron-ion interaction potential (EIIP) index value to each amino acid residue contained in the amino acid sequence of the HA protein or fragment; (iii) subjecting the resultant EIIP index values to discrete Fourier transformation (DFT); (iv) generating an informational spectrum (IS) of the at least one HA protein or fragment based on the EIIP index values;

(2)(i) obtaining an amino acid sequence of a peptide or peptides; (ii) assigning an EIIP index value to each amino acid residue contained in the amino acid sequence of the peptide or peptides; (iii) subjecting the resultant EIIP index values to discrete Fourier transformation (DFT); (iv) generating an informational spectrum (IS) of each peptide based on the EIIP index values;

(3) comparing the IS of the at least one HA protein or fragment generated in (1)(iv) to the IS of the peptide or peptides generated in (2)(iv); and (4) identifying the peptide or peptides whose IS overlap with the IS of the at least one HA protein or fragment, and based thereon identifying the peptide or peptides as one being capable of eliciting an immune response against the HA protein or fragment.

5. The method of claim 4, which further includes any of the following:

(i) synthesizing at least one of the identified peptides;

(ii) synthesizing at least one of the identified peptides and assessing its immunogenicity or ability to generate antibodies that specifically bind to said at least one HA protein;

(iii) producing an immunologic composition comprising at least one of the peptides identified by any of the foregoing methods; and (iv) generating a cross-spectrum (CS) based on the IS of the at least one HA protein generated in (1)(iv) and the IS of the peptide or peptides generated in (2)(iv) according to any of the foregoing methods to identify a common frequency component.

6. A method for the treatment or prevention of influenza virus infection in a subject, comprising administering a therapeutically effective amount of an isolated synthetic peptide or an immunologic composition according to claim 1 or a therapeutically effective amount of an antibody or antigen binding fragment that binds thereto in a subject in need thereof, wherein the immunologic composition or the synthetic peptide or the antibody or antigen binding fragment thereof effectively treats or prevents influenza infection in the subject, optionally a human subject.

7. A method of eliciting an immune response by administering an immunologic composition of claim 1.

8. A method for producing the immunologic composition of claim 1, comprising (i) obtaining the synthetic peptide, and (ii) admixing the synthetic peptide with a pharmaceutically acceptable carrier and/or excipient and/or adjuvant.

* * * * *

SEQUENCE LISTING

```
<160> NUMBER OF SEQ ID NOS: 109

<210> SEQ ID NO 1
<211> LENGTH: 34
<212> TYPE: PRT
<213> ORGANISM: Artificial Sequence
<220> FEATURE:
<223> OTHER INFORMATION: synthetic peptide

<400> SEQUENCE: 1

Cys Asp Glu Asp Gly Val Lys Pro Leu Ile Leu Arg Asp Cys Cys Val
1               5                   10                  15

Ala Gly Trp Leu Leu Gly Asn His Ser Cys Asp Val Phe Ile Asn Val
            20                  25                  30

Pro Glu

<210> SEQ ID NO 2
<211> LENGTH: 34
<212> TYPE: PRT
<213> ORGANISM: Artificial Sequence
<220> FEATURE:
<223> OTHER INFORMATION: synthetic peptide

<400> SEQUENCE: 2

Cys Asp Glu Asp Gly Val His Pro Leu Ile Leu Arg Asp Cys Cys Val
1               5                   10                  15

Ala Ile Tyr Leu Leu Gly Asn His Ser Cys Asp Val Phe Ile Leu Val
            20                  25                  30

Pro Glu

<210> SEQ ID NO 3
```

```
<211> LENGTH: 34
<212> TYPE: PRT
<213> ORGANISM: Artificial Sequence
<220> FEATURE:
<223> OTHER INFORMATION: synthetic peptide

<400> SEQUENCE: 3

Cys Asp Glu Asp Gly Asn His Pro Leu Ile Leu Arg Asp Cys Cys Val
1               5                   10                  15

Ala Ile Tyr Leu Leu Asn Asn His Ser Cys Asp Val Phe Ile Leu Glu
            20                  25                  30

Pro Leu

<210> SEQ ID NO 4
<211> LENGTH: 34
<212> TYPE: PRT
<213> ORGANISM: Artificial Sequence
<220> FEATURE:
<223> OTHER INFORMATION: synthetic peptide

<400> SEQUENCE: 4

Cys Asp Glu Asp Gly Ile His Pro Leu Ile Leu Arg Asp Cys Cys Val
1               5                   10                  15

Ala Ile Tyr Leu Leu Ile Asn His Ser Cys Asp Val Phe Ile Leu Asn
            20                  25                  30

Pro Gly

<210> SEQ ID NO 5
<211> LENGTH: 34
<212> TYPE: PRT
<213> ORGANISM: Artificial Sequence
<220> FEATURE:
<223> OTHER INFORMATION: synthetic peptide

<400> SEQUENCE: 5

Cys Asp Leu Asp Gly Leu His Pro Leu Ile Leu Arg Asp Cys Ser Val
1               5                   10                  15

Ala Asn Tyr Leu Leu Ile Asn Pro Met Cys Asp Glu Phe Ile Leu Glu
            20                  25                  30

Pro Leu

<210> SEQ ID NO 6
<211> LENGTH: 34
<212> TYPE: PRT
<213> ORGANISM: Artificial Sequence
<220> FEATURE:
<223> OTHER INFORMATION: synthetic peptide

<400> SEQUENCE: 6

Ser Asp Gly Asp Ile Asn Lys Pro Leu Leu Val Thr Asp Ser Cys Asn
1               5                   10                  15

Lys Asn Tyr Leu Leu Asn Ile His Ser Cys Asp Val Thr Asn Ile Ile
            20                  25                  30

Pro Asn

<210> SEQ ID NO 7
<211> LENGTH: 34
<212> TYPE: PRT
<213> ORGANISM: Artificial Sequence
<220> FEATURE:
<223> OTHER INFORMATION: synthetic peptide

<400> SEQUENCE: 7
```

```
Gln Asp Leu Asp Ile Asn Lys Pro Leu Leu Asn Thr Asp Gln Met Leu
1               5                   10                  15

Lys Asn Tyr Leu Leu Asn Ile Pro Gln Gln Asp Leu Thr Asn Ile Ile
            20                  25                  30

Pro Asn

<210> SEQ ID NO 8
<211> LENGTH: 34
<212> TYPE: PRT
<213> ORGANISM: Artificial Sequence
<220> FEATURE:
<223> OTHER INFORMATION: synthetic peptide

<400> SEQUENCE: 8

Glu Glu Leu Lys Lys Leu Leu Cys Arg Ile Asn Lys Phe Glu Lys Ile
1               5                   10                  15

Ser Ile Ile Pro Lys Gly Ser Trp Ser Asp His Glu Ala Cys Gly Val
            20                  25                  30

Ser Cys

<210> SEQ ID NO 9
<211> LENGTH: 34
<212> TYPE: PRT
<213> ORGANISM: Artificial Sequence
<220> FEATURE:
<223> OTHER INFORMATION: synthetic peptide

<400> SEQUENCE: 9

Glu Gly Leu Lys His Leu Leu Ser Arg Ile Leu His Phe Ile His Ile
1               5                   10                  15

Gln Ile Ile Pro Lys Asn Gln Tyr Ser Asp His Ile Ala Ser Gly Asn
            20                  25                  30

Ser Ser

<210> SEQ ID NO 10
<211> LENGTH: 34
<212> TYPE: PRT
<213> ORGANISM: Artificial Sequence
<220> FEATURE:
<223> OTHER INFORMATION: synthetic peptide

<400> SEQUENCE: 10

Glu Gly Leu Lys Lys Leu Leu Cys Arg Ile Ile Lys Phe Gly His Ile
1               5                   10                  15

Ser Ile Ile Pro Lys Gly Met Tyr Ser Asp His Gly Ala Cys Gly Glu
            20                  25                  30

Ser Cys

<210> SEQ ID NO 11
<211> LENGTH: 34
<212> TYPE: PRT
<213> ORGANISM: Artificial Sequence
<220> FEATURE:
<223> OTHER INFORMATION: synthetic peptide

<400> SEQUENCE: 11

Glu Asn Leu Lys Lys Leu Leu Cys Arg Leu Ile Lys Phe Asn His Ile
1               5                   10                  15

Ser Ile Ile Pro Lys Gly Gln Tyr Ser Asp His Asn Ala Cys Gly Gly
            20                  25                  30
```

Ser Cys

<210> SEQ ID NO 12
<211> LENGTH: 34
<212> TYPE: PRT
<213> ORGANISM: Artificial Sequence
<220> FEATURE:
<223> OTHER INFORMATION: synthetic peptide

<400> SEQUENCE: 12

Glu Ile Leu Lys Lys Leu Leu Cys Arg Leu Ile Lys Phe Ile His Ile
1               5                   10                  15

Ser Ile Ile Pro Lys Gly Gln Tyr Ser Asp His Ile Ala Cys Gly Asn
            20                  25                  30

Ser Cys

<210> SEQ ID NO 13
<211> LENGTH: 34
<212> TYPE: PRT
<213> ORGANISM: Artificial Sequence
<220> FEATURE:
<223> OTHER INFORMATION: synthetic peptide

<400> SEQUENCE: 13

Gly Leu Val Ala Pro Asn Val Met Thr Val Leu Pro Thr Gly Lys Val
1               5                   10                  15

Met Val Leu Pro Ala Val Gln Tyr Met Asp Pro Gly Ala Met Val Ile
            20                  25                  30

Met Met

<210> SEQ ID NO 14
<211> LENGTH: 34
<212> TYPE: PRT
<213> ORGANISM: Artificial Sequence
<220> FEATURE:
<223> OTHER INFORMATION: synthetic peptide

<400> SEQUENCE: 14

Gly Gly Val Ala His Val Val Cys Thr Val Val His Thr Gly Ala Val
1               5                   10                  15

Cys Val Val Pro Ala Val Met Trp Met Asp Pro Gly Ala Ser Val Val
            20                  25                  30

Met Ser

<210> SEQ ID NO 15
<211> LENGTH: 42
<212> TYPE: PRT
<213> ORGANISM: Artificial Sequence
<220> FEATURE:
<223> OTHER INFORMATION: synthetic peptide

<400> SEQUENCE: 15

Gly Ala Asn Asn Thr Cys Leu Pro Phe Gln Asn Asn His Pro Ile Thr
1               5                   10                  15

Ile Gly Ala Cys Pro Lys Trp Val Lys Cys Thr Lys Asn Arg Leu Ala
            20                  25                  30

Thr Gly Leu Arg Asn Ile His Ser Ile Gln
                35                  40

<210> SEQ ID NO 16
<211> LENGTH: 42
<212> TYPE: PRT

<213> ORGANISM: Artificial Sequence
<220> FEATURE:
<223> OTHER INFORMATION: synthetic peptide

<400> SEQUENCE: 16

Leu Ala Asn Asn Thr Cys Leu Pro Phe Gln Asn Asn His Pro Ile Thr
1               5                   10                  15

Ile Leu Ala Cys Pro Lys Trp Val Lys Cys Thr Lys Asn Arg Leu Ala
            20                  25                  30

Thr Gly Leu Arg Asn Ile His Ser Ile Gln
        35                  40

<210> SEQ ID NO 17
<211> LENGTH: 42
<212> TYPE: PRT
<213> ORGANISM: Artificial Sequence
<220> FEATURE:
<223> OTHER INFORMATION: synthetic peptide

<400> SEQUENCE: 17

Ile Ala Gly Asn Thr Cys Leu Pro Phe Gln Asn Gly His Pro Ile Thr
1               5                   10                  15

Ile Ile Ala Cys Pro Lys Trp Val Lys Cys Thr Lys Gly Arg Leu Ala
            20                  25                  30

Thr Gly Leu Arg Asn Ile His Ser Ile Gln
        35                  40

<210> SEQ ID NO 18
<211> LENGTH: 42
<212> TYPE: PRT
<213> ORGANISM: Artificial Sequence
<220> FEATURE:
<223> OTHER INFORMATION: synthetic peptide

<400> SEQUENCE: 18

Asn Ala Glu Asn Thr Cys Leu Pro Phe Gln Asn Glu His Pro Ile Thr
1               5                   10                  15

Val Asn Ala Cys Pro Lys Trp Val Lys Cys Thr Lys Glu Arg Leu Ala
            20                  25                  30

Thr Gly Leu Arg Asn Ile His Ser Ile Gln
        35                  40

<210> SEQ ID NO 19
<211> LENGTH: 42
<212> TYPE: PRT
<213> ORGANISM: Artificial Sequence
<220> FEATURE:
<223> OTHER INFORMATION: synthetic peptide

<400> SEQUENCE: 19

Leu Ala Val Asn Thr Cys Leu Pro Phe Gln Asn Val His Pro Ile Thr
1               5                   10                  15

Val Leu Ala Cys Pro Lys Trp Val Lys Cys Thr Lys Val Arg Leu Ala
            20                  25                  30

Thr Gly Leu Arg Asn Ile His Ser Ile Gln
        35                  40

<210> SEQ ID NO 20
<211> LENGTH: 42
<212> TYPE: PRT
<213> ORGANISM: Artificial Sequence
<220> FEATURE:
<223> OTHER INFORMATION: synthetic peptide

<400> SEQUENCE: 20

Leu Ala Val Val Thr Gln Val Pro Thr Met Leu Val Pro Pro Val Thr
1               5                   10                  15

Val Val Ala Met Pro Ala Trp Val Lys Met Thr Lys Val Thr Val Ala
            20                  25                  30

Thr Val Val Thr Val Asn Pro Met Val Gln
        35                  40

<210> SEQ ID NO 21
<211> LENGTH: 42
<212> TYPE: PRT
<213> ORGANISM: Artificial Sequence
<220> FEATURE:
<223> OTHER INFORMATION: synthetic peptide

<400> SEQUENCE: 21

Leu Ala Val Val Thr Cys Val Pro Thr Met Leu Gly His Pro Val Thr
1               5                   10                  15

Val Val Ala Met Pro Ala Trp Val Lys Ser Thr Lys Glu Thr Val Ala
            20                  25                  30

Thr Val Val Thr Val Asn His Met Val Gln
        35                  40

<210> SEQ ID NO 22
<211> LENGTH: 22
<212> TYPE: PRT
<213> ORGANISM: Artificial Sequence
<220> FEATURE:
<223> OTHER INFORMATION: synthetic peptide

<400> SEQUENCE: 22

Thr Leu Lys Thr Ile Ile Thr Leu Leu Pro Met Leu Met Met Thr Val
1               5                   10                  15

Gly Thr Leu Ala Val Ala
            20

<210> SEQ ID NO 23
<211> LENGTH: 22
<212> TYPE: PRT
<213> ORGANISM: Artificial Sequence
<220> FEATURE:
<223> OTHER INFORMATION: synthetic peptide

<400> SEQUENCE: 23

Thr Leu Ala Phe Ile Ile Thr Glu Leu Pro Ser Leu Met Cys Arg Val
1               5                   10                  15

Gly Arg Leu Ala Val Ala
            20

<210> SEQ ID NO 24
<211> LENGTH: 22
<212> TYPE: PRT
<213> ORGANISM: Artificial Sequence
<220> FEATURE:
<223> OTHER INFORMATION: synthetic peptide

<400> SEQUENCE: 24

Thr Leu Ala Thr Ile Ile Thr Val Leu Pro Met Leu Gln Met Thr Asn
1               5                   10                  15

Ile Thr Val Lys Val Ala
            20

<210> SEQ ID NO 25
<211> LENGTH: 22
<212> TYPE: PRT
<213> ORGANISM: Artificial Sequence
<220> FEATURE:
<223> OTHER INFORMATION: synthetic peptide

<400> SEQUENCE: 25

```
Thr Val Ala Phe Val Val Arg Glu Val Pro Ser Val Met Cys Arg Val
1               5                   10                  15

Val Arg Glu Ala Val Ala
            20
```

<210> SEQ ID NO 26
<211> LENGTH: 34
<212> TYPE: PRT
<213> ORGANISM: Artificial Sequence
<220> FEATURE:
<223> OTHER INFORMATION: synthetic peptide

<400> SEQUENCE: 26

```
Cys Asp Glu Asp Gly Val Lys Pro Leu Ile Leu Arg Asp Cys Cys Val
1               5                   10                  15

Ala Gly Trp Leu Leu Gly Asn His Ser Cys Asp Val Phe Ile Asn Val
            20                  25                  30

Pro Glu
```

<210> SEQ ID NO 27
<211> LENGTH: 34
<212> TYPE: PRT
<213> ORGANISM: Artificial Sequence
<220> FEATURE:
<223> OTHER INFORMATION: synthetic peptide

<400> SEQUENCE: 27

```
Cys Asp Glu Asp Gly Val His Pro Leu Ile Leu Arg Asp Cys Cys Val
1               5                   10                  15

Ala Ile Tyr Leu Leu Gly Asn His Ser Cys Asp Val Phe Ile Leu Val
            20                  25                  30

Pro Glu
```

<210> SEQ ID NO 28
<211> LENGTH: 34
<212> TYPE: PRT
<213> ORGANISM: Artificial Sequence
<220> FEATURE:
<223> OTHER INFORMATION: synthetic peptide

<400> SEQUENCE: 28

```
Cys Asp Glu Asp Gly Asn His Pro Leu Ile Leu Arg Asp Cys Cys Val
1               5                   10                  15

Ala Ile Tyr Leu Leu Asn Asn His Ser Cys Asp Val Phe Ile Leu Glu
            20                  25                  30

Pro Leu
```

<210> SEQ ID NO 29
<211> LENGTH: 34
<212> TYPE: PRT
<213> ORGANISM: Artificial Sequence
<220> FEATURE:
<223> OTHER INFORMATION: synthetic peptide

<400> SEQUENCE: 29

```
Cys Asp Glu Asp Gly Ile His Pro Leu Ile Leu Arg Asp Cys Cys Val
1               5                   10                  15

Ala Ile Tyr Leu Leu Ile Asn His Ser Cys Asp Val Phe Ile Leu Asn
            20                  25                  30

Pro Gly
```

<210> SEQ ID NO 30
<211> LENGTH: 34
<212> TYPE: PRT
<213> ORGANISM: Artificial Sequence
<220> FEATURE:
<223> OTHER INFORMATION: synthetic peptide

<400> SEQUENCE: 30

```
Cys Asp Leu Asp Gly Leu His Pro Leu Ile Leu Arg Asp Cys Ser Val
1               5                   10                  15

Ala Asn Tyr Leu Leu Ile Asn Pro Met Cys Asp Glu Phe Ile Leu Glu
            20                  25                  30

Pro Leu
```

<210> SEQ ID NO 31
<211> LENGTH: 34
<212> TYPE: PRT
<213> ORGANISM: Artificial Sequence
<220> FEATURE:
<223> OTHER INFORMATION: synthetic peptide

<400> SEQUENCE: 31

```
Glu Glu Leu Lys Lys Leu Leu Cys Arg Ile Asn Lys Phe Glu Lys Ile
1               5                   10                  15

Ser Ile Ile Pro Lys Gly Ser Trp Ser Asp His Glu Ala Cys Gly Val
            20                  25                  30

Ser Cys
```

<210> SEQ ID NO 32
<211> LENGTH: 34
<212> TYPE: PRT
<213> ORGANISM: Artificial Sequence
<220> FEATURE:
<223> OTHER INFORMATION: synthetic peptide

<400> SEQUENCE: 32

```
Glu Gly Leu Lys His Leu Leu Ser Arg Ile Leu His Phe Ile His Ile
1               5                   10                  15

Gln Ile Ile Pro Lys Asn Gln Tyr Ser Asp His Ile Ala Ser Gly Asn
            20                  25                  30

Ser Ser
```

<210> SEQ ID NO 33
<211> LENGTH: 34
<212> TYPE: PRT
<213> ORGANISM: Artificial Sequence
<220> FEATURE:
<223> OTHER INFORMATION: synthetic peptide

<400> SEQUENCE: 33

```
Glu Gly Leu Lys Lys Leu Leu Cys Arg Ile Ile Lys Phe Gly His Ile
1               5                   10                  15

Ser Ile Ile Pro Lys Gly Met Tyr Ser Asp His Gly Ala Cys Gly Glu
            20                  25                  30
```

Ser Cys

<210> SEQ ID NO 34
<211> LENGTH: 34
<212> TYPE: PRT
<213> ORGANISM: Artificial Sequence
<220> FEATURE:
<223> OTHER INFORMATION: synthetic peptide

<400> SEQUENCE: 34

Glu Asn Leu Lys Lys Leu Leu Cys Arg Leu Ile Lys Phe Asn His Ile
1               5                   10                  15

Ser Ile Ile Pro Lys Gly Gln Tyr Ser Asp His Asn Ala Cys Gly Gly
            20                  25                  30

Ser Cys

<210> SEQ ID NO 35
<211> LENGTH: 34
<212> TYPE: PRT
<213> ORGANISM: Artificial Sequence
<220> FEATURE:
<223> OTHER INFORMATION: synthetic peptide

<400> SEQUENCE: 35

Glu Ile Leu Lys Lys Leu Leu Cys Arg Leu Ile Lys Phe Ile His Ile
1               5                   10                  15

Ser Ile Ile Pro Lys Gly Gln Tyr Ser Asp His Ile Ala Cys Gly Asn
            20                  25                  30

Ser Cys

<210> SEQ ID NO 36
<211> LENGTH: 42
<212> TYPE: PRT
<213> ORGANISM: Artificial Sequence
<220> FEATURE:
<223> OTHER INFORMATION: synthetic peptide

<400> SEQUENCE: 36

Gly Ala Asn Asn Thr Cys Leu Pro Phe Gln Asn Asn His Pro Ile Thr
1               5                   10                  15

Ile Gly Ala Cys Pro Lys Trp Val Lys Cys Thr Lys Asn Arg Leu Ala
            20                  25                  30

Thr Gly Leu Arg Asn Ile His Ser Ile Gln
            35                  40

<210> SEQ ID NO 37
<211> LENGTH: 42
<212> TYPE: PRT
<213> ORGANISM: Artificial Sequence
<220> FEATURE:
<223> OTHER INFORMATION: synthetic peptide

<400> SEQUENCE: 37

Leu Ala Asn Asn Thr Cys Leu Pro Phe Gln Asn Asn His Pro Ile Thr
1               5                   10                  15

Ile Leu Ala Cys Pro Lys Trp Val Lys Cys Thr Lys Asn Arg Leu Ala
            20                  25                  30

Thr Gly Leu Arg Asn Ile His Ser Ile Gln
            35                  40

<210> SEQ ID NO 38
<211> LENGTH: 42

```
<212> TYPE: PRT
<213> ORGANISM: Artificial Sequence
<220> FEATURE:
<223> OTHER INFORMATION: synthetic peptide

<400> SEQUENCE: 38

Ile Ala Gly Asn Thr Cys Leu Pro Phe Gln Asn Gly His Pro Ile Thr
1               5                   10                  15

Ile Ile Ala Cys Pro Lys Trp Val Lys Cys Thr Lys Gly Arg Leu Ala
            20                  25                  30

Thr Gly Leu Arg Asn Ile His Ser Ile Gln
        35                  40

<210> SEQ ID NO 39
<211> LENGTH: 42
<212> TYPE: PRT
<213> ORGANISM: Artificial Sequence
<220> FEATURE:
<223> OTHER INFORMATION: synthetic peptide

<400> SEQUENCE: 39

Asn Ala Glu Asn Thr Cys Leu Pro Phe Gln Asn Glu His Pro Ile Thr
1               5                   10                  15

Val Asn Ala Cys Pro Lys Trp Val Lys Cys Thr Lys Glu Arg Leu Ala
            20                  25                  30

Thr Gly Leu Arg Asn Ile His Ser Ile Gln
        35                  40

<210> SEQ ID NO 40
<211> LENGTH: 42
<212> TYPE: PRT
<213> ORGANISM: Artificial Sequence
<220> FEATURE:
<223> OTHER INFORMATION: synthetic peptide

<400> SEQUENCE: 40

Leu Ala Val Asn Thr Cys Leu Pro Phe Gln Asn Val His Pro Ile Thr
1               5                   10                  15

Val Leu Ala Cys Pro Lys Trp Val Lys Cys Thr Lys Val Arg Leu Ala
            20                  25                  30

Thr Gly Leu Arg Asn Ile His Ser Ile Gln
        35                  40

<210> SEQ ID NO 41
<211> LENGTH: 22
<212> TYPE: PRT
<213> ORGANISM: Artificial Sequence
<220> FEATURE:
<223> OTHER INFORMATION: synthetic peptide

<400> SEQUENCE: 41

Thr Leu Lys Thr Ile Ile Thr Leu Leu Pro Met Leu Met Met Thr Val
1               5                   10                  15

Gly Thr Leu Ala Val Ala
            20

<210> SEQ ID NO 42
<211> LENGTH: 22
<212> TYPE: PRT
<213> ORGANISM: Artificial Sequence
<220> FEATURE:
<223> OTHER INFORMATION: synthetic peptide

<400> SEQUENCE: 42
```

```
Thr Leu Ala Phe Ile Ile Thr Glu Leu Pro Ser Leu Met Cys Arg Val
1               5                   10                  15

Gly Arg Leu Ala Val Ala
            20
```

<210> SEQ ID NO 43
<211> LENGTH: 34
<212> TYPE: PRT
<213> ORGANISM: Artificial Sequence
<220> FEATURE:
<223> OTHER INFORMATION: synthetic peptide

<400> SEQUENCE: 43

```
Ser Asp Gly Asp Ile Asn Lys Pro Leu Leu Val Thr Asp Ser Cys Asn
1               5                   10                  15

Lys Asn Tyr Leu Leu Asn Ile His Ser Cys Asp Val Thr Asn Ile Ile
            20                  25                  30

Pro Asn
```

<210> SEQ ID NO 44
<211> LENGTH: 34
<212> TYPE: PRT
<213> ORGANISM: Artificial Sequence
<220> FEATURE:
<223> OTHER INFORMATION: synthetic peptide

<400> SEQUENCE: 44

```
Gln Asp Leu Asp Ile Asn Lys Pro Leu Leu Asn Thr Asp Gln Met Leu
1               5                   10                  15

Lys Asn Tyr Leu Leu Asn Ile Pro Gln Gln Asp Leu Thr Asn Ile Ile
            20                  25                  30

Pro Asn
```

<210> SEQ ID NO 45
<211> LENGTH: 34
<212> TYPE: PRT
<213> ORGANISM: Artificial Sequence
<220> FEATURE:
<223> OTHER INFORMATION: synthetic peptide

<400> SEQUENCE: 45

```
Gly Leu Val Ala Pro Asn Val Met Thr Val Leu Pro Thr Gly Lys Val
1               5                   10                  15

Met Val Leu Pro Ala Val Gln Tyr Met Asp Pro Gly Ala Met Val Ile
            20                  25                  30

Met Met
```

<210> SEQ ID NO 46
<211> LENGTH: 34
<212> TYPE: PRT
<213> ORGANISM: Artificial Sequence
<220> FEATURE:
<223> OTHER INFORMATION: synthetic peptide

<400> SEQUENCE: 46

```
Gly Gly Val Ala His Val Val Cys Thr Val His Thr Gly Ala Val
1               5                   10                  15

Cys Val Val Pro Ala Val Met Trp Met Asp Pro Gly Ala Ser Val Val
            20                  25                  30

Met Ser
```

<210> SEQ ID NO 47
<211> LENGTH: 42
<212> TYPE: PRT
<213> ORGANISM: Artificial Sequence
<220> FEATURE:
<223> OTHER INFORMATION: synthetic peptide

<400> SEQUENCE: 47

```
Leu Ala Val Val Thr Gln Val Pro Thr Met Leu Val Pro Pro Val Thr
1               5                   10                  15

Val Val Ala Met Pro Ala Trp Val Lys Met Thr Lys Val Thr Val Ala
            20                  25                  30

Thr Val Thr Val Asn Pro Met Val Gln
        35                  40
```

<210> SEQ ID NO 48
<211> LENGTH: 42
<212> TYPE: PRT
<213> ORGANISM: Artificial Sequence
<220> FEATURE:
<223> OTHER INFORMATION: synthetic peptide

<400> SEQUENCE: 48

```
Leu Ala Val Val Thr Cys Val Pro Thr Met Leu Gly His Pro Val Thr
1               5                   10                  15

Val Val Ala Met Pro Ala Trp Val Lys Ser Thr Lys Glu Thr Val Ala
            20                  25                  30

Thr Val Thr Val Asn His Met Val Gln
        35                  40
```

<210> SEQ ID NO 49
<211> LENGTH: 22
<212> TYPE: PRT
<213> ORGANISM: Artificial Sequence
<220> FEATURE:
<223> OTHER INFORMATION: synthetic peptide

<400> SEQUENCE: 49

```
Thr Leu Ala Thr Ile Ile Thr Val Leu Pro Met Leu Gln Met Thr Asn
1               5                   10                  15

Ile Thr Val Lys Val Ala
            20
```

<210> SEQ ID NO 50
<211> LENGTH: 22
<212> TYPE: PRT
<213> ORGANISM: Artificial Sequence
<220> FEATURE:
<223> OTHER INFORMATION: synthetic peptide

<400> SEQUENCE: 50

```
Thr Val Ala Phe Val Val Arg Glu Val Pro Ser Val Met Cys Arg Val
1               5                   10                  15

Val Arg Glu Ala Val Ala
            20
```

<210> SEQ ID NO 51
<211> LENGTH: 34
<212> TYPE: PRT
<213> ORGANISM: Artificial Sequence
<220> FEATURE:
<223> OTHER INFORMATION: synthetic peptide

<400> SEQUENCE: 51

```
Cys Asp Glu Asp Gly Val Lys Pro Leu Ile Leu Arg Asp Cys Cys Val
1               5                   10                  15

Ala Gly Trp Leu Leu Gly Asn His Ser Cys Asp Val Phe Ile Asn Val
            20                  25                  30

Pro Glu

<210> SEQ ID NO 52
<211> LENGTH: 34
<212> TYPE: PRT
<213> ORGANISM: Artificial Sequence
<220> FEATURE:
<223> OTHER INFORMATION: synthetic peptide

<400> SEQUENCE: 52

Cys Asp Glu Asp Gly Val His Pro Leu Ile Leu Arg Asp Cys Cys Val
1               5                   10                  15

Ala Ile Tyr Leu Leu Gly Asn His Ser Cys Asp Val Phe Ile Leu Val
            20                  25                  30

Pro Glu

<210> SEQ ID NO 53
<211> LENGTH: 34
<212> TYPE: PRT
<213> ORGANISM: Artificial Sequence
<220> FEATURE:
<223> OTHER INFORMATION: synthetic peptide

<400> SEQUENCE: 53

Cys Asp Glu Asp Gly Asn His Pro Leu Ile Leu Arg Asp Cys Cys Val
1               5                   10                  15

Ala Ile Tyr Leu Leu Asn Asn His Ser Cys Asp Val Phe Ile Leu Glu
            20                  25                  30

Pro Leu

<210> SEQ ID NO 54
<211> LENGTH: 34
<212> TYPE: PRT
<213> ORGANISM: Artificial Sequence
<220> FEATURE:
<223> OTHER INFORMATION: synthetic peptide

<400> SEQUENCE: 54

Cys Asp Glu Asp Gly Ile His Pro Leu Ile Leu Arg Asp Cys Cys Val
1               5                   10                  15

Ala Ile Tyr Leu Leu Ile Asn His Ser Cys Asp Val Phe Ile Leu Asn
            20                  25                  30

Pro Gly

<210> SEQ ID NO 55
<211> LENGTH: 34
<212> TYPE: PRT
<213> ORGANISM: Artificial Sequence
<220> FEATURE:
<223> OTHER INFORMATION: synthetic peptide

<400> SEQUENCE: 55

Cys Asp Leu Asp Gly Leu His Pro Leu Ile Leu Arg Asp Cys Ser Val
1               5                   10                  15

Ala Asn Tyr Leu Leu Ile Asn Pro Met Cys Asp Glu Phe Ile Leu Glu
            20                  25                  30
```

Pro Leu

<210> SEQ ID NO 56
<211> LENGTH: 34
<212> TYPE: PRT
<213> ORGANISM: Artificial Sequence
<220> FEATURE:
<223> OTHER INFORMATION: synthetic peptide

<400> SEQUENCE: 56

Ser Asp Gly Asp Ile Asn Lys Pro Leu Leu Val Thr Asp Ser Cys Asn
1               5                   10                  15

Lys Asn Tyr Leu Leu Asn Ile His Ser Cys Asp Val Thr Asn Ile Ile
            20                  25                  30

Pro Asn

<210> SEQ ID NO 57
<211> LENGTH: 34
<212> TYPE: PRT
<213> ORGANISM: Artificial Sequence
<220> FEATURE:
<223> OTHER INFORMATION: synthetic peptide

<400> SEQUENCE: 57

Gln Asp Leu Asp Ile Asn Lys Pro Leu Leu Asn Thr Asp Gln Met Leu
1               5                   10                  15

Lys Asn Tyr Leu Leu Asn Ile Pro Gln Gln Asp Leu Thr Asn Ile Ile
            20                  25                  30

Pro Asn

<210> SEQ ID NO 58
<211> LENGTH: 34
<212> TYPE: PRT
<213> ORGANISM: Artificial Sequence
<220> FEATURE:
<223> OTHER INFORMATION: synthetic peptide

<400> SEQUENCE: 58

Glu Glu Leu Lys Lys Leu Leu Cys Arg Ile Asn Lys Phe Glu Lys Ile
1               5                   10                  15

Ser Ile Ile Pro Lys Gly Ser Trp Ser Asp His Glu Ala Cys Gly Val
            20                  25                  30

Ser Cys

<210> SEQ ID NO 59
<211> LENGTH: 34
<212> TYPE: PRT
<213> ORGANISM: Artificial Sequence
<220> FEATURE:
<223> OTHER INFORMATION: synthetic peptide

<400> SEQUENCE: 59

Glu Gly Leu Lys His Leu Leu Ser Arg Ile Leu His Phe Ile His Ile
1               5                   10                  15

Gln Ile Ile Pro Lys Asn Gln Tyr Ser Asp His Ile Ala Ser Gly Asn
            20                  25                  30

Ser Ser

<210> SEQ ID NO 60
<211> LENGTH: 34
<212> TYPE: PRT
<213> ORGANISM: Artificial Sequence
<220> FEATURE:
<223> OTHER INFORMATION: synthetic peptide

<400> SEQUENCE: 60

Glu Gly Leu Lys Lys Leu Leu Cys Arg Ile Ile Lys Phe Gly His Ile
1               5                   10                  15

Ser Ile Ile Pro Lys Gly Met Tyr Ser Asp His Gly Ala Cys Gly Glu
            20                  25                  30

Ser Cys

<210> SEQ ID NO 61
<211> LENGTH: 34
<212> TYPE: PRT
<213> ORGANISM: Artificial Sequence
<220> FEATURE:
<223> OTHER INFORMATION: synthetic peptide

<400> SEQUENCE: 61

Glu Asn Leu Lys Lys Leu Leu Cys Arg Leu Ile Lys Phe Asn His Ile
1               5                   10                  15

Ser Ile Ile Pro Lys Gly Gln Tyr Ser Asp His Asn Ala Cys Gly Gly
            20                  25                  30

Ser Cys

<210> SEQ ID NO 62
<211> LENGTH: 34
<212> TYPE: PRT
<213> ORGANISM: Artificial Sequence
<220> FEATURE:
<223> OTHER INFORMATION: synthetic peptide

<400> SEQUENCE: 62

Glu Ile Leu Lys Lys Leu Leu Cys Arg Leu Ile Lys Phe Ile His Ile
1               5                   10                  15

Ser Ile Ile Pro Lys Gly Gln Tyr Ser Asp His Ile Ala Cys Gly Asn
            20                  25                  30

Ser Cys

<210> SEQ ID NO 63
<211> LENGTH: 34
<212> TYPE: PRT
<213> ORGANISM: Artificial Sequence
<220> FEATURE:
<223> OTHER INFORMATION: synthetic peptide

<400> SEQUENCE: 63

Gly Leu Val Ala Pro Asn Val Met Thr Val Leu Pro Thr Gly Lys Val
1               5                   10                  15

Met Val Leu Pro Ala Val Gln Tyr Met Asp Pro Gly Ala Met Val Ile
            20                  25                  30

Met Met

<210> SEQ ID NO 64
<211> LENGTH: 34
<212> TYPE: PRT
<213> ORGANISM: Artificial Sequence
<220> FEATURE:
<223> OTHER INFORMATION: synthetic peptide

<400> SEQUENCE: 64

Gly Gly Val Ala His Val Val Cys Thr Val Val His Thr Gly Ala Val
1               5                   10                  15

```
Cys Val Val Pro Ala Val Met Trp Met Asp Pro Gly Ala Ser Val Val
            20                  25                  30

Met Ser

<210> SEQ ID NO 65
<211> LENGTH: 42
<212> TYPE: PRT
<213> ORGANISM: Artificial Sequence
<220> FEATURE:
<223> OTHER INFORMATION: synthetic peptide

<400> SEQUENCE: 65

Gly Ala Asn Asn Thr Cys Leu Pro Phe Gln Asn Asn His Pro Ile Thr
1               5                   10                  15

Ile Gly Ala Cys Pro Lys Trp Val Lys Cys Thr Lys Asn Arg Leu Ala
            20                  25                  30

Thr Gly Leu Arg Asn Ile His Ser Ile Gln
        35                  40

<210> SEQ ID NO 66
<211> LENGTH: 42
<212> TYPE: PRT
<213> ORGANISM: Artificial Sequence
<220> FEATURE:
<223> OTHER INFORMATION: synthetic peptide

<400> SEQUENCE: 66

Leu Ala Asn Asn Thr Cys Leu Pro Phe Gln Asn Asn His Pro Ile Thr
1               5                   10                  15

Ile Leu Ala Cys Pro Lys Trp Val Lys Cys Thr Lys Asn Arg Leu Ala
            20                  25                  30

Thr Gly Leu Arg Asn Ile His Ser Ile Gln
        35                  40

<210> SEQ ID NO 67
<211> LENGTH: 42
<212> TYPE: PRT
<213> ORGANISM: Artificial Sequence
<220> FEATURE:
<223> OTHER INFORMATION: synthetic peptide

<400> SEQUENCE: 67

Ile Ala Gly Asn Thr Cys Leu Pro Phe Gln Asn Gly His Pro Ile Thr
1               5                   10                  15

Ile Ile Ala Cys Pro Lys Trp Val Lys Cys Thr Lys Gly Arg Leu Ala
            20                  25                  30

Thr Gly Leu Arg Asn Ile His Ser Ile Gln
        35                  40

<210> SEQ ID NO 68
<211> LENGTH: 42
<212> TYPE: PRT
<213> ORGANISM: Artificial Sequence
<220> FEATURE:
<223> OTHER INFORMATION: synthetic peptide

<400> SEQUENCE: 68

Asn Ala Glu Asn Thr Cys Leu Pro Phe Gln Asn Glu His Pro Ile Thr
1               5                   10                  15

Val Asn Ala Cys Pro Lys Trp Val Lys Cys Thr Lys Glu Arg Leu Ala
            20                  25                  30
```

Thr Gly Leu Arg Asn Ile His Ser Ile Gln
        35                  40

<210> SEQ ID NO 69
<211> LENGTH: 42
<212> TYPE: PRT
<213> ORGANISM: Artificial Sequence
<220> FEATURE:
<223> OTHER INFORMATION: synthetic peptide

<400> SEQUENCE: 69

Leu Ala Val Asn Thr Cys Leu Pro Phe Gln Asn Val His Pro Ile Thr
1               5                   10                  15

Val Leu Ala Cys Pro Lys Trp Val Lys Cys Thr Lys Val Arg Leu Ala
            20                  25                  30

Thr Gly Leu Arg Asn Ile His Ser Ile Gln
        35                  40

<210> SEQ ID NO 70
<211> LENGTH: 42
<212> TYPE: PRT
<213> ORGANISM: Artificial Sequence
<220> FEATURE:
<223> OTHER INFORMATION: synthetic peptide

<400> SEQUENCE: 70

Leu Ala Val Val Thr Gln Val Pro Thr Met Leu Val Pro Pro Val Thr
1               5                   10                  15

Val Val Ala Met Pro Ala Trp Val Lys Met Thr Lys Val Thr Val Ala
            20                  25                  30

Thr Val Val Thr Val Asn Pro Met Val Gln
        35                  40

<210> SEQ ID NO 71
<211> LENGTH: 42
<212> TYPE: PRT
<213> ORGANISM: Artificial Sequence
<220> FEATURE:
<223> OTHER INFORMATION: synthetic peptide

<400> SEQUENCE: 71

Leu Ala Val Val Thr Cys Val Pro Thr Met Leu Gly His Pro Val Thr
1               5                   10                  15

Val Val Ala Met Pro Ala Trp Val Lys Ser Thr Lys Glu Thr Val Ala
            20                  25                  30

Thr Val Val Thr Val Asn His Met Val Gln
        35                  40

<210> SEQ ID NO 72
<211> LENGTH: 22
<212> TYPE: PRT
<213> ORGANISM: Artificial Sequence
<220> FEATURE:
<223> OTHER INFORMATION: synthetic peptide

<400> SEQUENCE: 72

Thr Leu Lys Thr Ile Ile Thr Leu Leu Pro Met Leu Met Thr Val
1               5                   10                  15

Gly Thr Leu Ala Val Ala
            20

<210> SEQ ID NO 73
<211> LENGTH: 22

```
<212> TYPE: PRT
<213> ORGANISM: Artificial Sequence
<220> FEATURE:
<223> OTHER INFORMATION: synthetic peptide

<400> SEQUENCE: 73

Thr Leu Ala Phe Ile Ile Thr Glu Leu Pro Ser Leu Met Cys Arg Val
1               5                   10                  15

Gly Arg Leu Ala Val Ala
            20

<210> SEQ ID NO 74
<211> LENGTH: 22
<212> TYPE: PRT
<213> ORGANISM: Artificial Sequence
<220> FEATURE:
<223> OTHER INFORMATION: synthetic peptide

<400> SEQUENCE: 74

Thr Leu Ala Thr Ile Ile Thr Val Leu Pro Met Leu Gln Met Thr Asn
1               5                   10                  15

Ile Thr Val Lys Val Ala
            20

<210> SEQ ID NO 75
<211> LENGTH: 22
<212> TYPE: PRT
<213> ORGANISM: Artificial Sequence
<220> FEATURE:
<223> OTHER INFORMATION: synthetic peptide

<400> SEQUENCE: 75

Thr Val Ala Phe Val Val Arg Glu Val Pro Ser Val Met Cys Arg Val
1               5                   10                  15

Val Arg Glu Ala Val Ala
            20

<210> SEQ ID NO 76
<211> LENGTH: 34
<212> TYPE: PRT
<213> ORGANISM: Artificial Sequence
<220> FEATURE:
<223> OTHER INFORMATION: synthetic peptide

<400> SEQUENCE: 76

Cys Asp Glu Asp Gly Val Lys Pro Leu Ile Leu Arg Asp Cys Cys Val
1               5                   10                  15

Ala Gly Trp Leu Leu Gly Asn His Ser Cys Asp Val Phe Ile Asn Val
            20                  25                  30

Pro Glu

<210> SEQ ID NO 77
<211> LENGTH: 34
<212> TYPE: PRT
<213> ORGANISM: Artificial Sequence
<220> FEATURE:
<223> OTHER INFORMATION: synthetic peptide

<400> SEQUENCE: 77

Cys Asp Glu Asp Gly Val His Pro Leu Ile Leu Arg Asp Cys Cys Val
1               5                   10                  15

Ala Ile Tyr Leu Leu Gly Asn His Ser Cys Asp Val Phe Ile Leu Val
            20                  25                  30
```

Pro Glu

<210> SEQ ID NO 78
<211> LENGTH: 34
<212> TYPE: PRT
<213> ORGANISM: Artificial Sequence
<220> FEATURE:
<223> OTHER INFORMATION: synthetic peptide

<400> SEQUENCE: 78

Cys Asp Glu Asp Gly Asn His Pro Leu Ile Leu Arg Asp Cys Cys Val
1               5                   10                  15

Ala Ile Tyr Leu Leu Asn Asn His Ser Cys Asp Val Phe Ile Leu Glu
            20                  25                  30

Pro Leu

<210> SEQ ID NO 79
<211> LENGTH: 34
<212> TYPE: PRT
<213> ORGANISM: Artificial Sequence
<220> FEATURE:
<223> OTHER INFORMATION: synthetic peptide

<400> SEQUENCE: 79

Cys Asp Glu Asp Gly Ile His Pro Leu Ile Leu Arg Asp Cys Cys Val
1               5                   10                  15

Ala Ile Tyr Leu Leu Ile Asn His Ser Cys Asp Val Phe Ile Leu Asn
            20                  25                  30

Pro Gly

<210> SEQ ID NO 80
<211> LENGTH: 34
<212> TYPE: PRT
<213> ORGANISM: Artificial Sequence
<220> FEATURE:
<223> OTHER INFORMATION: synthetic peptide

<400> SEQUENCE: 80

Cys Asp Leu Asp Gly Leu His Pro Leu Ile Leu Arg Asp Cys Ser Val
1               5                   10                  15

Ala Asn Tyr Leu Leu Ile Asn Pro Met Cys Asp Glu Phe Ile Leu Glu
            20                  25                  30

Pro Leu

<210> SEQ ID NO 81
<211> LENGTH: 34
<212> TYPE: PRT
<213> ORGANISM: Artificial Sequence
<220> FEATURE:
<223> OTHER INFORMATION: synthetic peptide

<400> SEQUENCE: 81

Glu Glu Leu Lys Lys Leu Leu Cys Arg Ile Asn Lys Phe Glu Lys Ile
1               5                   10                  15

Ser Ile Ile Pro Lys Gly Ser Trp Ser Asp His Glu Ala Cys Gly Val
            20                  25                  30

Ser Cys

<210> SEQ ID NO 82
<211> LENGTH: 34
<212> TYPE: PRT
<213> ORGANISM: Artificial Sequence

```
<220> FEATURE:
<223> OTHER INFORMATION: synthetic peptide

<400> SEQUENCE: 82

Glu Gly Leu Lys His Leu Leu Ser Arg Ile Leu His Phe Ile His Ile
1               5                   10                  15

Gln Ile Ile Pro Lys Asn Gln Tyr Ser Asp His Ile Ala Ser Gly Asn
            20                  25                  30

Ser Ser

<210> SEQ ID NO 83
<211> LENGTH: 34
<212> TYPE: PRT
<213> ORGANISM: Artificial Sequence
<220> FEATURE:
<223> OTHER INFORMATION: synthetic peptide

<400> SEQUENCE: 83

Glu Gly Leu Lys Lys Leu Leu Cys Arg Ile Ile Lys Phe Gly His Ile
1               5                   10                  15

Ser Ile Ile Pro Lys Gly Met Tyr Ser Asp His Gly Ala Cys Gly Glu
            20                  25                  30

Ser Cys

<210> SEQ ID NO 84
<211> LENGTH: 34
<212> TYPE: PRT
<213> ORGANISM: Artificial Sequence
<220> FEATURE:
<223> OTHER INFORMATION: synthetic peptide

<400> SEQUENCE: 84

Glu Asn Leu Lys Lys Leu Leu Cys Arg Leu Ile Lys Phe Asn His Ile
1               5                   10                  15

Ser Ile Ile Pro Lys Gly Gln Tyr Ser Asp His Asn Ala Cys Gly Gly
            20                  25                  30

Ser Cys

<210> SEQ ID NO 85
<211> LENGTH: 34
<212> TYPE: PRT
<213> ORGANISM: Artificial Sequence
<220> FEATURE:
<223> OTHER INFORMATION: synthetic peptide

<400> SEQUENCE: 85

Glu Ile Leu Lys Lys Leu Leu Cys Arg Leu Ile Lys Phe Ile His Ile
1               5                   10                  15

Ser Ile Ile Pro Lys Gly Gln Tyr Ser Asp His Ile Ala Cys Gly Asn
            20                  25                  30

Ser Cys

<210> SEQ ID NO 86
<211> LENGTH: 42
<212> TYPE: PRT
<213> ORGANISM: Artificial Sequence
<220> FEATURE:
<223> OTHER INFORMATION: synthetic peptide

<400> SEQUENCE: 86

Gly Ala Asn Asn Thr Cys Leu Pro Phe Gln Asn Asn His Pro Ile Thr
1               5                   10                  15
```

```
Ile Gly Ala Cys Pro Lys Trp Val Lys Cys Thr Lys Asn Arg Leu Ala
            20                  25                  30

Thr Gly Leu Arg Asn Ile His Ser Ile Gln
        35                  40

<210> SEQ ID NO 87
<211> LENGTH: 42
<212> TYPE: PRT
<213> ORGANISM: Artificial Sequence
<220> FEATURE:
<223> OTHER INFORMATION: synthetic peptide

<400> SEQUENCE: 87

Leu Ala Asn Asn Thr Cys Leu Pro Phe Gln Asn Asn His Pro Ile Thr
1               5                   10                  15

Ile Leu Ala Cys Pro Lys Trp Val Lys Cys Thr Lys Asn Arg Leu Ala
            20                  25                  30

Thr Gly Leu Arg Asn Ile His Ser Ile Gln
        35                  40

<210> SEQ ID NO 88
<211> LENGTH: 42
<212> TYPE: PRT
<213> ORGANISM: Artificial Sequence
<220> FEATURE:
<223> OTHER INFORMATION: synthetic peptide

<400> SEQUENCE: 88

Ile Ala Gly Asn Thr Cys Leu Pro Phe Gln Asn Gly His Pro Ile Thr
1               5                   10                  15

Ile Ile Ala Cys Pro Lys Trp Val Lys Cys Thr Lys Gly Arg Leu Ala
            20                  25                  30

Thr Gly Leu Arg Asn Ile His Ser Ile Gln
        35                  40

<210> SEQ ID NO 89
<211> LENGTH: 42
<212> TYPE: PRT
<213> ORGANISM: Artificial Sequence
<220> FEATURE:
<223> OTHER INFORMATION: synthetic peptide

<400> SEQUENCE: 89

Asn Ala Glu Asn Thr Cys Leu Pro Phe Gln Asn Glu His Pro Ile Thr
1               5                   10                  15

Val Asn Ala Cys Pro Lys Trp Val Lys Cys Thr Lys Glu Arg Leu Ala
            20                  25                  30

Thr Gly Leu Arg Asn Ile His Ser Ile Gln
        35                  40

<210> SEQ ID NO 90
<211> LENGTH: 42
<212> TYPE: PRT
<213> ORGANISM: Artificial Sequence
<220> FEATURE:
<223> OTHER INFORMATION: synthetic peptide

<400> SEQUENCE: 90

Leu Ala Val Asn Thr Cys Leu Pro Phe Gln Asn Val His Pro Ile Thr
1               5                   10                  15

Val Leu Ala Cys Pro Lys Trp Val Lys Cys Thr Lys Val Arg Leu Ala
            20                  25                  30
```

```
Thr Gly Leu Arg Asn Ile His Ser Ile Gln
        35                  40

<210> SEQ ID NO 91
<211> LENGTH: 22
<212> TYPE: PRT
<213> ORGANISM: Artificial Sequence
<220> FEATURE:
<223> OTHER INFORMATION: synthetic peptide

<400> SEQUENCE: 91

Thr Leu Lys Thr Ile Ile Thr Leu Leu Pro Met Leu Met Met Thr Val
1               5                   10                  15

Gly Thr Leu Ala Val Ala
            20

<210> SEQ ID NO 92
<211> LENGTH: 22
<212> TYPE: PRT
<213> ORGANISM: Artificial Sequence
<220> FEATURE:
<223> OTHER INFORMATION: synthetic peptide

<400> SEQUENCE: 92

Thr Leu Ala Phe Ile Ile Thr Glu Leu Pro Ser Leu Met Cys Arg Val
1               5                   10                  15

Gly Arg Leu Ala Val Ala
            20

<210> SEQ ID NO 93
<211> LENGTH: 34
<212> TYPE: PRT
<213> ORGANISM: Artificial Sequence
<220> FEATURE:
<223> OTHER INFORMATION: synthetic peptide

<400> SEQUENCE: 93

Ser Asp Gly Asp Ile Asn Lys Pro Leu Leu Val Thr Asp Ser Cys Asn
1               5                   10                  15

Lys Asn Tyr Leu Leu Asn Ile His Ser Cys Asp Val Thr Asn Ile Ile
            20                  25                  30

Pro Asn

<210> SEQ ID NO 94
<211> LENGTH: 34
<212> TYPE: PRT
<213> ORGANISM: Artificial Sequence
<220> FEATURE:
<223> OTHER INFORMATION: synthetic peptide

<400> SEQUENCE: 94

Gln Asp Leu Asp Ile Asn Lys Pro Leu Leu Asn Thr Asp Gln Met Leu
1               5                   10                  15

Lys Asn Tyr Leu Leu Asn Ile Pro Gln Gln Asp Leu Thr Asn Ile Ile
            20                  25                  30

Pro Asn

<210> SEQ ID NO 95
<211> LENGTH: 34
<212> TYPE: PRT
<213> ORGANISM: Artificial Sequence
<220> FEATURE:
<223> OTHER INFORMATION: synthetic peptide
```

-continued

<400> SEQUENCE: 95

Gly Leu Val Ala Pro Asn Val Met Thr Val Leu Pro Thr Gly Lys Val
1               5                   10                  15

Met Val Leu Pro Ala Val Gln Tyr Met Asp Pro Gly Ala Met Val Ile
            20                  25                  30

Met Met

<210> SEQ ID NO 96
<211> LENGTH: 34
<212> TYPE: PRT
<213> ORGANISM: Artificial Sequence
<220> FEATURE:
<223> OTHER INFORMATION: synthetic peptide

<400> SEQUENCE: 96

Gly Gly Val Ala His Val Val Cys Thr Val Val His Thr Gly Ala Val
1               5                   10                  15

Cys Val Val Pro Ala Val Met Trp Met Asp Pro Gly Ala Ser Val Val
            20                  25                  30

Met Ser

<210> SEQ ID NO 97
<211> LENGTH: 42
<212> TYPE: PRT
<213> ORGANISM: Artificial Sequence
<220> FEATURE:
<223> OTHER INFORMATION: synthetic peptide

<400> SEQUENCE: 97

Leu Ala Val Val Thr Gln Val Pro Thr Met Leu Val Pro Pro Val Thr
1               5                   10                  15

Val Val Ala Met Pro Ala Trp Val Lys Met Thr Lys Val Thr Val Ala
            20                  25                  30

Thr Val Val Thr Val Asn Pro Met Val Gln
            35                  40

<210> SEQ ID NO 98
<211> LENGTH: 42
<212> TYPE: PRT
<213> ORGANISM: Artificial Sequence
<220> FEATURE:
<223> OTHER INFORMATION: synthetic peptide

<400> SEQUENCE: 98

Leu Ala Val Val Thr Cys Val Pro Thr Met Leu Gly His Pro Val Thr
1               5                   10                  15

Val Val Ala Met Pro Ala Trp Val Lys Ser Thr Lys Glu Thr Val Ala
            20                  25                  30

Thr Val Val Thr Val Asn His Met Val Gln
            35                  40

<210> SEQ ID NO 99
<211> LENGTH: 22
<212> TYPE: PRT
<213> ORGANISM: Artificial Sequence
<220> FEATURE:
<223> OTHER INFORMATION: synthetic peptide

<400> SEQUENCE: 99

Thr Leu Ala Thr Ile Ile Thr Val Leu Pro Met Leu Gln Met Thr Asn
1               5                   10                  15

```
Ile Thr Val Lys Val Ala
            20

<210> SEQ ID NO 100
<211> LENGTH: 22
<212> TYPE: PRT
<213> ORGANISM: Artificial Sequence
<220> FEATURE:
<223> OTHER INFORMATION: synthetic peptide

<400> SEQUENCE: 100

Thr Val Ala Phe Val Val Arg Glu Val Pro Ser Val Met Cys Arg Val
1               5                   10                  15

Val Arg Glu Ala Val Ala
            20

<210> SEQ ID NO 101
<211> LENGTH: 330
<212> TYPE: PRT
<213> ORGANISM: Artificial Sequence
<220> FEATURE:
<223> OTHER INFORMATION: H5N1

<400> SEQUENCE: 101

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Asn Ser Trp Ser Ser His Glu Ala Ser
        115                 120                 125

Leu Gly Val Ser Ser Ala Cys Pro Tyr Gln Gly Lys Ser Ser Phe Phe
    130                 135                 140

Arg Asn Val Val Trp Leu Ile Lys Lys Asn Asn Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Asn Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
```

260                 265                 270
Asn Cys Asn Thr Lys Cys Gln Thr Pro Met Gly Ala Ile Asn Ser Ser
            275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Arg Arg Lys Lys Arg
                325                 330

<210> SEQ ID NO 102
<211> LENGTH: 34
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa is Met, Ser, Gln or Cys
<220> FEATURE:
<221> NAME/KEY: misc_feature
<222> LOCATION: (2)..(2)
<223> OTHER INFORMATION: Xaa is Asp
<220> FEATURE:
<221> NAME/KEY: misc_feature
<222> LOCATION: (3)..(3)
<223> OTHER INFORMATION: Xaa is Val, Leu, Ile, Asn, Gly or Glu
<220> FEATURE:
<221> NAME/KEY: misc_feature
<222> LOCATION: (4)..(4)
<223> OTHER INFORMATION: Xaa is Asp
<220> FEATURE:
<221> NAME/KEY: misc_feature
<222> LOCATION: (5)..(5)
<223> OTHER INFORMATION: Xaa is Val, Leu, Ile, Asn or Gly
<220> FEATURE:
<221> NAME/KEY: misc_feature
<222> LOCATION: (6)..(6)
<223> OTHER INFORMATION: Xaa is Val, Leu, Ile, Asn or Gly
<220> FEATURE:
<221> NAME/KEY: misc_feature
<222> LOCATION: (7)..(7)
<223> OTHER INFORMATION: Xaa is Pro, His, Ala or Lys
<220> FEATURE:
<221> NAME/KEY: misc_feature
<222> LOCATION: (8)..(8)
<223> OTHER INFORMATION: Xaa is Pro or His
<220> FEATURE:
<221> NAME/KEY: misc_feature
<222> LOCATION: (9)..(9)
<223> OTHER INFORMATION: Xaa is Val, Leu, Ile, Asn or Gly
<220> FEATURE:
<221> NAME/KEY: misc_feature
<222> LOCATION: (10)..(10)
<223> OTHER INFORMATION: Xaa is Val, Leu, Ile, Asn or Gly
<220> FEATURE:
<221> NAME/KEY: misc_feature
<222> LOCATION: (11)..(11)
<223> OTHER INFORMATION: Xaa is Val, Leu, Ile, Asn or Gly
<220> FEATURE:
<221> NAME/KEY: misc_feature
<222> LOCATION: (12)..(12)
<223> OTHER INFORMATION: Xaa is Thr, Phe or Arg
<220> FEATURE:
<221> NAME/KEY: misc_feature
<222> LOCATION: (13)..(13)
<223> OTHER INFORMATION: Xaa is Asp
<220> FEATURE:
<221> NAME/KEY: misc_feature
<222> LOCATION: (14)..(14)
<223> OTHER INFORMATION: Xaa is Met, Ser, Gln or Cys
<220> FEATURE:
<221> NAME/KEY: misc_feature

```
<222> LOCATION: (15)..(15)
<223> OTHER INFORMATION: Xaa is Met, Ser, Gln or Cys
<220> FEATURE:
<221> NAME/KEY: misc_feature
<222> LOCATION: (16)..(16)
<223> OTHER INFORMATION: Xaa is Val, Leu, Ile, Asn or Gly
<220> FEATURE:
<221> NAME/KEY: misc_feature
<222> LOCATION: (17)..(17)
<223> OTHER INFORMATION: Xaa is Ala or Lys
<220> FEATURE:
<221> NAME/KEY: misc_feature
<222> LOCATION: (18)..(18)
<223> OTHER INFORMATION: Xaa is Val, Leu, Ile, Asn, Gly or Glu
<220> FEATURE:
<221> NAME/KEY: misc_feature
<222> LOCATION: (19)..(19)
<223> OTHER INFORMATION: Xaa is Trp or Tyr
<220> FEATURE:
<221> NAME/KEY: misc_feature
<222> LOCATION: (20)..(20)
<223> OTHER INFORMATION: Xaa is Val, Leu, Ile, Asn or Gly
<220> FEATURE:
<221> NAME/KEY: misc_feature
<222> LOCATION: (21)..(21)
<223> OTHER INFORMATION: Xaa is Val, Leu, Ile, Asn or Gly
<220> FEATURE:
<221> NAME/KEY: misc_feature
<222> LOCATION: (22)..(22)
<223> OTHER INFORMATION: Xaa is Val, Leu, Ile, Asn, Gly or Glu
<220> FEATURE:
<221> NAME/KEY: misc_feature
<222> LOCATION: (23)..(23)
<223> OTHER INFORMATION: Xaa is Val, Leu, Ile, Asn or Gly
<220> FEATURE:
<221> NAME/KEY: misc_feature
<222> LOCATION: (24)..(24)
<223> OTHER INFORMATION: Xaa is Pro or His
<220> FEATURE:
<221> NAME/KEY: misc_feature
<222> LOCATION: (25)..(25)
<223> OTHER INFORMATION: Xaa is Met, Ser, Gln or Cys
<220> FEATURE:
<221> NAME/KEY: misc_feature
<222> LOCATION: (26)..(26)
<223> OTHER INFORMATION: Xaa is Met, Ser, Gln or Cys
<220> FEATURE:
<221> NAME/KEY: misc_feature
<222> LOCATION: (27)..(27)
<223> OTHER INFORMATION: Xaa is Asp
<220> FEATURE:
<221> NAME/KEY: misc_feature
<222> LOCATION: (28)..(28)
<223> OTHER INFORMATION: Xaa is Val, Leu, Ile, Asn, Gly or Glu
<220> FEATURE:
<221> NAME/KEY: misc_feature
<222> LOCATION: (29)..(29)
<223> OTHER INFORMATION: Xaa is Thr, Phe or Arg
<220> FEATURE:
<221> NAME/KEY: misc_feature
<222> LOCATION: (30)..(30)
<223> OTHER INFORMATION: Xaa is Val, Leu, Ile, Asn or Gly
<220> FEATURE:
<221> NAME/KEY: misc_feature
<222> LOCATION: (31)..(31)
<223> OTHER INFORMATION: Xaa is Val, Leu, Ile, Asn or Gly
<220> FEATURE:
<221> NAME/KEY: misc_feature
<222> LOCATION: (32)..(32)
<223> OTHER INFORMATION: Xaa is Val, Leu, Ile, Asn, Gly or Glu
<220> FEATURE:
<221> NAME/KEY: misc_feature
<222> LOCATION: (33)..(33)
<223> OTHER INFORMATION: Xaa is Pro or His
<220> FEATURE:
<221> NAME/KEY: misc_feature
<222> LOCATION: (34)..(34)
<223> OTHER INFORMATION: Xaa is Val, Leu, Ile, Asn, Gly or Glu
```

<400> SEQUENCE: 102

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa

<210> SEQ ID NO 103
<211> LENGTH: 34
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa is independently Val, Leu, Ile, Asn, Gly or
      Glu
<220> FEATURE:
<221> NAME/KEY: misc_feature
<222> LOCATION: (6)..(6)
<223> OTHER INFORMATION: Xaa is independently Val, Leu, Ile, Asn, Gly or
      Glu
<220> FEATURE:
<221> NAME/KEY: misc_feature
<222> LOCATION: (7)..(7)
<223> OTHER INFORMATION: Xaa is Pro, His, Ala or Lys
<220> FEATURE:
<221> NAME/KEY: misc_feature
<222> LOCATION: (18)..(18)
<223> OTHER INFORMATION: Xaa is independently Val, Leu, Ile, Asn, Gly or
      Glu
<220> FEATURE:
<221> NAME/KEY: misc_feature
<222> LOCATION: (22)..(22)
<223> OTHER INFORMATION: Xaa is independently Val, Leu, Ile, Asn, Gly or
      Glu
<220> FEATURE:
<221> NAME/KEY: misc_feature
<222> LOCATION: (31)..(32)
<223> OTHER INFORMATION: Xaa is independently Val, Leu, Ile, Asn, Gly or
      Glu
<220> FEATURE:
<221> NAME/KEY: misc_feature
<222> LOCATION: (34)..(34)
<223> OTHER INFORMATION: Xaa is independently Val, Leu, Ile, Asn, Gly or
      Glu

<400> SEQUENCE: 103

Cys Asp Xaa Asp Gly Xaa Xaa Pro Leu Ile Leu Arg Asp Cys Cys Val
1               5                   10                  15

Ala Xaa Tyr Leu Leu Xaa Asn His Ser Cys Asp Val Phe Ile Xaa Xaa
                20                  25                  30

Pro Xaa

<210> SEQ ID NO 104
<211> LENGTH: 34
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa is Gly or Glu
<220> FEATURE:
<221> NAME/KEY: misc_feature
<222> LOCATION: (2)..(2)
<223> OTHER INFORMATION: Xaa is Val, Leu, Ile, Asn, Gly or Glu
<220> FEATURE:
<221> NAME/KEY: misc_feature

```
-continued

<222> LOCATION: (3)..(3)
<223> OTHER INFORMATION: Xaa is Val, Leu, Ile, Asn or Gly
<220> FEATURE:
<221> NAME/KEY: misc_feature
<222> LOCATION: (4)..(4)
<223> OTHER INFORMATION: Xaa is Ala or Lys
<220> FEATURE:
<221> NAME/KEY: misc_feature
<222> LOCATION: (5)..(5)
<223> OTHER INFORMATION: Xaa is Pro, His, or Lys
<220> FEATURE:
<221> NAME/KEY: misc_feature
<222> LOCATION: (6)..(6)
<223> OTHER INFORMATION: Xaa is Val, Leu, Ile, Asn or Gly
<220> FEATURE:
<221> NAME/KEY: misc_feature
<222> LOCATION: (7)..(7)
<223> OTHER INFORMATION: Xaa is Val, Leu, Ile, Asn or Gly
<220> FEATURE:
<221> NAME/KEY: misc_feature
<222> LOCATION: (8)..(8)
<223> OTHER INFORMATION: Xaa is Met, Ser, Gln or Cys
<220> FEATURE:
<221> NAME/KEY: misc_feature
<222> LOCATION: (9)..(9)
<223> OTHER INFORMATION: Xaa is Thr, Phe or Arg
<220> FEATURE:
<221> NAME/KEY: misc_feature
<222> LOCATION: (10)..(10)
<223> OTHER INFORMATION: Xaa is Val, Leu, Ile, Asn or Gly
<220> FEATURE:
<221> NAME/KEY: misc_feature
<222> LOCATION: (11)..(11)
<223> OTHER INFORMATION: Xaa is Val, Leu, Ile, Asn or Gly
<220> FEATURE:
<221> NAME/KEY: misc_feature
<222> LOCATION: (12)..(12)
<223> OTHER INFORMATION: Xaa is Pro, His, or Lys
<220> FEATURE:
<221> NAME/KEY: misc_feature
<222> LOCATION: (13)..(13)
<223> OTHER INFORMATION: Xaa is Thr, Phe or Arg
<220> FEATURE:
<221> NAME/KEY: misc_feature
<222> LOCATION: (14)..(14)
<223> OTHER INFORMATION: Xaa is Val, Leu, Ile, Asn, Gly or Glu
<220> FEATURE:
<221> NAME/KEY: misc_feature
<222> LOCATION: (15)..(15)
<223> OTHER INFORMATION: Xaa is Pro, His, Ala or Lys
<220> FEATURE:
<221> NAME/KEY: misc_feature
<222> LOCATION: (16)..(16)
<223> OTHER INFORMATION: Xaa is Val, Leu, Ile, Asn or Gly
<220> FEATURE:
<221> NAME/KEY: misc_feature
<222> LOCATION: (17)..(17)
<223> OTHER INFORMATION: Xaa is Met, Ser, Gln or Cys
<220> FEATURE:
<221> NAME/KEY: misc_feature
<222> LOCATION: (18)..(18)
<223> OTHER INFORMATION: Xaa is Val, Leu, Ile, Asn or Gly
<220> FEATURE:
<221> NAME/KEY: misc_feature
<222> LOCATION: (19)..(19)
<223> OTHER INFORMATION: Xaa is Val, Leu, Ile, Asn or Gly
<220> FEATURE:
<221> NAME/KEY: misc_feature
<222> LOCATION: (20)..(20)
<223> OTHER INFORMATION: Xaa is Pro or His
<220> FEATURE:
<221> NAME/KEY: misc_feature
<222> LOCATION: (21)..(21)
<223> OTHER INFORMATION: Xaa is Ala or Lys
<220> FEATURE:
<221> NAME/KEY: misc_feature
<222> LOCATION: (22)..(22)
<223> OTHER INFORMATION: Xaa is Val, Leu, Ile, Asn or Gly
<220> FEATURE:
```

<221> NAME/KEY: misc_feature
<222> LOCATION: (23)..(23)
<223> OTHER INFORMATION: Xaa is Met, Ser, Gln or Cys
<220> FEATURE:
<221> NAME/KEY: misc_feature
<222> LOCATION: (24)..(24)
<223> OTHER INFORMATION: Xaa is Trp or Tyr
<220> FEATURE:
<221> NAME/KEY: misc_feature
<222> LOCATION: (25)..(25)
<223> OTHER INFORMATION: Xaa is Met, Ser, Gln or Cys
<220> FEATURE:
<221> NAME/KEY: misc_feature
<222> LOCATION: (26)..(26)
<223> OTHER INFORMATION: Xaa is Asp
<220> FEATURE:
<221> NAME/KEY: misc_feature
<222> LOCATION: (27)..(27)
<223> OTHER INFORMATION: Xaa is Pro or His
<220> FEATURE:
<221> NAME/KEY: misc_feature
<222> LOCATION: (28)..(28)
<223> OTHER INFORMATION: Xaa is Val, Leu, Ile, Asn, Gly or Glu
<220> FEATURE:
<221> NAME/KEY: misc_feature
<222> LOCATION: (29)..(29)
<223> OTHER INFORMATION: Xaa is Ala or Lys
<220> FEATURE:
<221> NAME/KEY: misc_feature
<222> LOCATION: (30)..(30)
<223> OTHER INFORMATION: Xaa is Met, Ser, Gln or Cys
<220> FEATURE:
<221> NAME/KEY: misc_feature
<222> LOCATION: (31)..(31)
<223> OTHER INFORMATION: Xaa is Val, Leu, Ile, Asn or Gly
<220> FEATURE:
<221> NAME/KEY: misc_feature
<222> LOCATION: (32)..(32)
<223> OTHER INFORMATION: Xaa is Val, Leu, Ile, Asn, Gly or Glu
<220> FEATURE:
<221> NAME/KEY: misc_feature
<222> LOCATION: (33)..(33)
<223> OTHER INFORMATION: Xaa is Met, Ser, Gln or Cys
<220> FEATURE:
<221> NAME/KEY: misc_feature
<222> LOCATION: (34)..(34)
<223> OTHER INFORMATION: Xaa is Met, Ser, Gln or Cys

<400> SEQUENCE: 104

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 105
<211> LENGTH: 42
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa is Val, Leu, Ile, Asn or Gly
<220> FEATURE:
<221> NAME/KEY: misc_feature
<222> LOCATION: (2)..(2)
<223> OTHER INFORMATION: Xaa is Ala or Lys
<220> FEATURE:
<221> NAME/KEY: misc_feature
<222> LOCATION: (3)..(3)
<223> OTHER INFORMATION: Xaa is Val, Leu, Ile, Asn, Gly or Glu
<220> FEATURE:
<221> NAME/KEY: misc_feature

```
<222> LOCATION: (4)..(4)
<223> OTHER INFORMATION: Xaa is Val, Leu, Ile, Asn or Gly
<220> FEATURE:
<221> NAME/KEY: misc_feature
<222> LOCATION: (5)..(5)
<223> OTHER INFORMATION: Xaa is Thr, Phe or Arg
<220> FEATURE:
<221> NAME/KEY: misc_feature
<222> LOCATION: (6)..(6)
<223> OTHER INFORMATION: Xaa is Met, Ser, Gln or Cys
<220> FEATURE:
<221> NAME/KEY: misc_feature
<222> LOCATION: (7)..(7)
<223> OTHER INFORMATION: Xaa is Val, Leu, Ile, Asn or Gly
<220> FEATURE:
<221> NAME/KEY: misc_feature
<222> LOCATION: (8)..(8)
<223> OTHER INFORMATION: Xaa is Pro or His
<220> FEATURE:
<221> NAME/KEY: misc_feature
<222> LOCATION: (9)..(9)
<223> OTHER INFORMATION: Xaa is Thr, Phe or Arg
<220> FEATURE:
<221> NAME/KEY: misc_feature
<222> LOCATION: (10)..(10)
<223> OTHER INFORMATION: Xaa is Met, Ser, Gln or Cys
<220> FEATURE:
<221> NAME/KEY: misc_feature
<222> LOCATION: (11)..(11)
<223> OTHER INFORMATION: Xaa is Val, Leu, Ile, Asn or Gly
<220> FEATURE:
<221> NAME/KEY: misc_feature
<222> LOCATION: (12)..(12)
<223> OTHER INFORMATION: Xaa is Val, Leu, Ile, Asn, Gly or Glu
<220> FEATURE:
<221> NAME/KEY: misc_feature
<222> LOCATION: (13)..(13)
<223> OTHER INFORMATION: Xaa is Pro or His
<220> FEATURE:
<221> NAME/KEY: misc_feature
<222> LOCATION: (14)..(14)
<223> OTHER INFORMATION: Xaa is Pro or His
<220> FEATURE:
<221> NAME/KEY: misc_feature
<222> LOCATION: (15)..(15)
<223> OTHER INFORMATION: Xaa is Val, Leu, Ile, Asn or Gly
<220> FEATURE:
<221> NAME/KEY: misc_feature
<222> LOCATION: (16)..(16)
<223> OTHER INFORMATION: Xaa is Thr, Phe or Arg
<220> FEATURE:
<221> NAME/KEY: misc_feature
<222> LOCATION: (17)..(17)
<223> OTHER INFORMATION: Xaa is Val, Leu, Ile, Asn or Gly
<220> FEATURE:
<221> NAME/KEY: misc_feature
<222> LOCATION: (18)..(18)
<223> OTHER INFORMATION: Xaa is Val, Leu, Ile, Asn or Gly
<220> FEATURE:
<221> NAME/KEY: misc_feature
<222> LOCATION: (19)..(19)
<223> OTHER INFORMATION: Xaa is Ala or Lys
<220> FEATURE:
<221> NAME/KEY: misc_feature
<222> LOCATION: (20)..(20)
<223> OTHER INFORMATION: Xaa is Met, Ser, Gln or Cys
<220> FEATURE:
<221> NAME/KEY: misc_feature
<222> LOCATION: (21)..(21)
<223> OTHER INFORMATION: Xaa is Pro or His
<220> FEATURE:
<221> NAME/KEY: misc_feature
<222> LOCATION: (22)..(22)
<223> OTHER INFORMATION: Xaa is Ala or Lys
<220> FEATURE:
<221> NAME/KEY: misc_feature
<222> LOCATION: (23)..(23)
<223> OTHER INFORMATION: Xaa is Trp or Tyr
<220> FEATURE:
```

-continued

<221> NAME/KEY: misc_feature
<222> LOCATION: (24)..(24)
<223> OTHER INFORMATION: Xaa is Val, Leu, Ile, Asn or Gly
<220> FEATURE:
<221> NAME/KEY: misc_feature
<222> LOCATION: (25)..(25)
<223> OTHER INFORMATION: Xaa is Ala or Lys
<220> FEATURE:
<221> NAME/KEY: misc_feature
<222> LOCATION: (26)..(26)
<223> OTHER INFORMATION: Xaa is Met, Ser, Gln or Cys
<220> FEATURE:
<221> NAME/KEY: misc_feature
<222> LOCATION: (27)..(27)
<223> OTHER INFORMATION: Xaa is Thr, Phe or Arg
<220> FEATURE:
<221> NAME/KEY: misc_feature
<222> LOCATION: (28)..(28)
<223> OTHER INFORMATION: Xaa is Ala or Lys
<220> FEATURE:
<221> NAME/KEY: misc_feature
<222> LOCATION: (29)..(29)
<223> OTHER INFORMATION: Xaa is Val, Leu, Ile, Asn, Gly, or Glu
<220> FEATURE:
<221> NAME/KEY: misc_feature
<222> LOCATION: (30)..(30)
<223> OTHER INFORMATION: Xaa is Thr, Phe or Arg
<220> FEATURE:
<221> NAME/KEY: misc_feature
<222> LOCATION: (31)..(31)
<223> OTHER INFORMATION: Xaa is Val, Leu, Ile, Asn or Gly
<220> FEATURE:
<221> NAME/KEY: misc_feature
<222> LOCATION: (32)..(32)
<223> OTHER INFORMATION: Xaa is Ala or Lys
<220> FEATURE:
<221> NAME/KEY: misc_feature
<222> LOCATION: (33)..(33)
<223> OTHER INFORMATION: Xaa is Thr, Phe or Arg
<220> FEATURE:
<221> NAME/KEY: misc_feature
<222> LOCATION: (34)..(34)
<223> OTHER INFORMATION: Xaa is Val, Leu, Ile, Asn or Gly
<220> FEATURE:
<221> NAME/KEY: misc_feature
<222> LOCATION: (35)..(35)
<223> OTHER INFORMATION: Xaa is Val, Leu, Ile, Asn or Gly
<220> FEATURE:
<221> NAME/KEY: misc_feature
<222> LOCATION: (36)..(36)
<223> OTHER INFORMATION: Xaa is Thr, Phe or Arg
<220> FEATURE:
<221> NAME/KEY: misc_feature
<222> LOCATION: (37)..(37)
<223> OTHER INFORMATION: Xaa is Val, Leu, Ile, Asn or Gly
<220> FEATURE:
<221> NAME/KEY: misc_feature
<222> LOCATION: (38)..(38)
<223> OTHER INFORMATION: Xaa is Val, Leu, Ile, Asn or Gly
<220> FEATURE:
<221> NAME/KEY: misc_feature
<222> LOCATION: (39)..(39)
<223> OTHER INFORMATION: Xaa is Pro or His
<220> FEATURE:
<221> NAME/KEY: misc_feature
<222> LOCATION: (40)..(40)
<223> OTHER INFORMATION: Xaa is Met, Ser, Gln or Cys
<220> FEATURE:
<221> NAME/KEY: misc_feature
<222> LOCATION: (41)..(41)
<223> OTHER INFORMATION: Xaa is Val, Leu, Ile, Asn or Gly
<220> FEATURE:
<221> NAME/KEY: misc_feature
<222> LOCATION: (42)..(42)
<223> OTHER INFORMATION: Xaa is Met, Ser, Gln or Cys

<400> SEQUENCE: 105

Xaa Xaa Xaa Xaa Xaa Xaa Xaa Xaa Xaa Xaa Xaa Xaa Xaa Xaa Xaa Xaa

```
1               5                   10                  15
Xaa Xaa Xaa Xaa Xaa Xaa Xaa Xaa Xaa Xaa Xaa Xaa Xaa Xaa Xaa
        20                  25                  30
Xaa Xaa Xaa Xaa Xaa Xaa Xaa Xaa Xaa Xaa
        35                  40

<210> SEQ ID NO 106
<211> LENGTH: 42
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa is independently Val, Leu, Ile, Asn, Gly,
      or Glu
<220> FEATURE:
<221> NAME/KEY: misc_feature
<222> LOCATION: (3)..(4)
<223> OTHER INFORMATION: Xaa is independently Val, Leu, Ile, Asn, Gly,
      or Glu
<220> FEATURE:
<221> NAME/KEY: misc_feature
<222> LOCATION: (7)..(7)
<223> OTHER INFORMATION: Xaa is independently Val, Leu, Ile, Asn, Gly,
      or Glu
<220> FEATURE:
<221> NAME/KEY: misc_feature
<222> LOCATION: (9)..(9)
<223> OTHER INFORMATION: Xaa is independently Thr, Phe or Arg
<220> FEATURE:
<221> NAME/KEY: misc_feature
<222> LOCATION: (10)..(10)
<223> OTHER INFORMATION: Xaa is independently Met, Ser, Gln or Cys
<220> FEATURE:
<221> NAME/KEY: misc_feature
<222> LOCATION: (11)..(12)
<223> OTHER INFORMATION: Xaa is independently Val, Leu, Ile, Asn, Gly,
      or Glu
<220> FEATURE:
<221> NAME/KEY: misc_feature
<222> LOCATION: (15)..(15)
<223> OTHER INFORMATION: Xaa is independently Val, Leu, Ile, Asn, Gly,
      or Glu
<220> FEATURE:
<221> NAME/KEY: misc_feature
<222> LOCATION: (17)..(18)
<223> OTHER INFORMATION: Xaa is independently Val, Leu, Ile, Asn, Gly,
      or Glu
<220> FEATURE:
<221> NAME/KEY: misc_feature
<222> LOCATION: (20)..(20)
<223> OTHER INFORMATION: Xaa is independently Met, Ser, Gln or Cys
<220> FEATURE:
<221> NAME/KEY: misc_feature
<222> LOCATION: (22)..(22)
<223> OTHER INFORMATION: Xaa is Pro, His, Ala or Lys
<220> FEATURE:
<221> NAME/KEY: misc_feature
<222> LOCATION: (26)..(26)
<223> OTHER INFORMATION: Xaa is independently Met, Ser, Gln or Cys
<220> FEATURE:
<221> NAME/KEY: misc_feature
<222> LOCATION: (29)..(29)
<223> OTHER INFORMATION: Xaa is independently Val, Leu, Ile, Asn, Gly,
      or Glu
<220> FEATURE:
<221> NAME/KEY: misc_feature
<222> LOCATION: (30)..(30)
<223> OTHER INFORMATION: Xaa is independently Thr, Phe or Arg
<220> FEATURE:
<221> NAME/KEY: misc_feature
<222> LOCATION: (31)..(31)
<223> OTHER INFORMATION: Xaa is independently Val, Leu, Ile, Asn, Gly,
      or Glu
```

-continued

```
<220> FEATURE:
<221> NAME/KEY: misc_feature
<222> LOCATION: (34)..(35)
<223> OTHER INFORMATION: Xaa is independently Val, Leu, Ile, Asn, Gly,
      or Glu
<220> FEATURE:
<221> NAME/KEY: misc_feature
<222> LOCATION: (36)..(36)
<223> OTHER INFORMATION: Xaa is independently Thr, Phe or Arg
<220> FEATURE:
<221> NAME/KEY: misc_feature
<222> LOCATION: (37)..(38)
<223> OTHER INFORMATION: Xaa is independently Val, Leu, Ile, Asn, Gly,
      or Glu
<220> FEATURE:
<221> NAME/KEY: misc_feature
<222> LOCATION: (40)..(40)
<223> OTHER INFORMATION: Xaa is independently Met, Ser, Gln or Cys
<220> FEATURE:
<221> NAME/KEY: misc_feature
<222> LOCATION: (41)..(41)
<223> OTHER INFORMATION: Xaa is independently Val, Leu, Ile, Asn, Gly,
      or Glu

<400> SEQUENCE: 106

Xaa Ala Xaa Xaa Thr Cys Xaa Pro Xaa Xaa Xaa Xaa His Pro Xaa Thr
1               5                   10                  15

Xaa Xaa Ala Xaa Pro Xaa Trp Val Lys Xaa Thr Lys Xaa Xaa Xaa Ala
            20                  25                  30

Thr Xaa Xaa Xaa Xaa Xaa His Xaa Xaa Gln
        35                  40

<210> SEQ ID NO 107
<211> LENGTH: 22
<212> TYPE: PRT
<213> ORGANISM: Artificial sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa is Thr, Phe or Arg
<220> FEATURE:
<221> NAME/KEY: misc_feature
<222> LOCATION: (2)..(2)
<223> OTHER INFORMATION: Xaa is Val, Leu, Ile, Asn or Gly
<220> FEATURE:
<221> NAME/KEY: misc_feature
<222> LOCATION: (3)..(3)
<223> OTHER INFORMATION: Xaa is Ala or Lys
<220> FEATURE:
<221> NAME/KEY: misc_feature
<222> LOCATION: (4)..(4)
<223> OTHER INFORMATION: Xaa is Thr, Phe or Arg
<220> FEATURE:
<221> NAME/KEY: misc_feature
<222> LOCATION: (5)..(5)
<223> OTHER INFORMATION: Xaa is Val, Leu, Ile, Asn or Gly
<220> FEATURE:
<221> NAME/KEY: misc_feature
<222> LOCATION: (6)..(6)
<223> OTHER INFORMATION: Xaa is Val, Leu, Ile, Asn or Gly
<220> FEATURE:
<221> NAME/KEY: misc_feature
<222> LOCATION: (7)..(7)
<223> OTHER INFORMATION: Xaa is Thr, Phe or Arg
<220> FEATURE:
<221> NAME/KEY: misc_feature
<222> LOCATION: (8)..(8)
<223> OTHER INFORMATION: Xaa is Val, Leu, Ile, Asn, Gly or Glu
<220> FEATURE:
<221> NAME/KEY: misc_feature
<222> LOCATION: (9)..(9)
<223> OTHER INFORMATION: Xaa is Val, Leu, Ile, Asn or Gly
<220> FEATURE:
```

```
<221> NAME/KEY: misc_feature
<222> LOCATION: (10)..(10)
<223> OTHER INFORMATION: Xaa is Pro or His
<220> FEATURE:
<221> NAME/KEY: misc_feature
<222> LOCATION: (11)..(11)
<223> OTHER INFORMATION: Xaa is Met, Ser, Gln or Cys
<220> FEATURE:
<221> NAME/KEY: misc_feature
<222> LOCATION: (12)..(12)
<223> OTHER INFORMATION: Xaa is Val, Leu, Ile, Asn or Gly
<220> FEATURE:
<221> NAME/KEY: misc_feature
<222> LOCATION: (13)..(13)
<223> OTHER INFORMATION: Xaa is Met, Ser, Gln or Cys
<220> FEATURE:
<221> NAME/KEY: misc_feature
<222> LOCATION: (14)..(14)
<223> OTHER INFORMATION: Xaa is Met, Ser, Gln or Cys
<220> FEATURE:
<221> NAME/KEY: misc_feature
<222> LOCATION: (15)..(15)
<223> OTHER INFORMATION: Xaa is Thr, Phe or Arg
<220> FEATURE:
<221> NAME/KEY: misc_feature
<222> LOCATION: (16)..(16)
<223> OTHER INFORMATION: Xaa is Val, Leu, Ile, Asn or Gly
<220> FEATURE:
<221> NAME/KEY: misc_feature
<222> LOCATION: (17)..(17)
<223> OTHER INFORMATION: Xaa is Val, Leu, Ile, Asn or Gly
<220> FEATURE:
<221> NAME/KEY: misc_feature
<222> LOCATION: (18)..(18)
<223> OTHER INFORMATION: Xaa is Thr, Phe or Arg
<220> FEATURE:
<221> NAME/KEY: misc_feature
<222> LOCATION: (19)..(19)
<223> OTHER INFORMATION: Xaa is Val, Leu, Ile, Asn, Gly or Glu
<220> FEATURE:
<221> NAME/KEY: misc_feature
<222> LOCATION: (20)..(20)
<223> OTHER INFORMATION: Xaa is Ala or Lys
<220> FEATURE:
<221> NAME/KEY: misc_feature
<222> LOCATION: (21)..(21)
<223> OTHER INFORMATION: Xaa is Val, Leu, Ile, Asn or Gly
<220> FEATURE:
<221> NAME/KEY: misc_feature
<222> LOCATION: (22)..(22)
<223> OTHER INFORMATION: Xaa is Ala or Lys

<400> SEQUENCE: 107

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 108
<211> LENGTH: 22
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa is independently Thr, Phe or Arg
<220> FEATURE:
<221> NAME/KEY: misc_feature
<222> LOCATION: (8)..(8)
<223> OTHER INFORMATION: Xaa is independently Val, Leu, Ile, Asn, Gly or
      Glu
<220> FEATURE:
<221> NAME/KEY: misc_feature
<222> LOCATION: (11)..(11)
```

```
<223> OTHER INFORMATION: Xaa is independently Met, Ser, Gln or Cys
<220> FEATURE:
<221> NAME/KEY: misc_feature
<222> LOCATION: (14)..(14)
<223> OTHER INFORMATION: Xaa is independently Met, Ser, Gln or Cys
<220> FEATURE:
<221> NAME/KEY: misc_feature
<222> LOCATION: (15)..(15)
<223> OTHER INFORMATION: Xaa is independently Thr, Phe or Arg
<220> FEATURE:
<221> NAME/KEY: misc_feature
<222> LOCATION: (17)..(17)
<223> OTHER INFORMATION: Xaa is independently Val, Leu, Ile, Asn, Gly or
      Glu
<220> FEATURE:
<221> NAME/KEY: misc_feature
<222> LOCATION: (18)..(18)
<223> OTHER INFORMATION: Xaa is independently Thr, Phe or Arg
<220> FEATURE:
<221> NAME/KEY: misc_feature
<222> LOCATION: (19)..(19)
<223> OTHER INFORMATION: Xaa is independently Val, Leu, Ile, Asn, Gly or
      Glu

<400> SEQUENCE: 108

Thr Leu Ala Xaa Ile Ile Thr Xaa Leu Pro Xaa Leu Met Xaa Xaa Val
1               5                   10                  15

Xaa Xaa Xaa Ala Val Ala
            20

<210> SEQ ID NO 109
<211> LENGTH: 34
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa is Val, Leu, Ile, Asn, Gly or Glu
<220> FEATURE:
<221> NAME/KEY: misc_feature
<222> LOCATION: (10)..(11)
<223> OTHER INFORMATION: Xaa is Val, Leu, Ile, Asn, Gly or Glu
<220> FEATURE:
<221> NAME/KEY: misc_feature
<222> LOCATION: (14)..(14)
<223> OTHER INFORMATION: Xaa is Val, Leu, Ile, Asn, Gly or Glu
<220> FEATURE:
<221> NAME/KEY: misc_feature
<222> LOCATION: (28)..(28)
<223> OTHER INFORMATION: Xaa is Val, Leu, Ile, Asn, Gly or Glu
<220> FEATURE:
<221> NAME/KEY: misc_feature
<222> LOCATION: (32)..(32)
<223> OTHER INFORMATION: Xaa is Val, Leu, Ile, Asn, Gly or Glu

<400> SEQUENCE: 109

Glu Xaa Leu Lys Lys Leu Leu Cys Arg Xaa Xaa Lys Phe Xaa His Ile
1               5                   10                  15

Ser Ile Ile Pro Lys Gly Gln Tyr Ser Asp His Xaa Ala Cys Gly Xaa
            20                  25                  30

Ser Cys
```